United States Patent
Funakubo et al.

(10) Patent No.: US 7,567,872 B2
(45) Date of Patent: Jul. 28, 2009

(54) FILM FORMING CONDITION DETERMINATION METHOD, FILM FORMING METHOD, AND FILM STRUCTURE MANUFACTURING METHOD

(75) Inventors: Hiroshi Funakubo, Yokohama (JP); Yoshihisa Honda, Matsudo (JP); Nataliya Nabatova-Gabain, Kyoto (JP); Asuka Terai, Kyoto (JP)

(73) Assignee: Horiba, Ltd., Kyoto (JP)

( * ) Notice: Subject to any disclaimer, the term of this patent is extended or adjusted under 35 U.S.C. 154(b) by 581 days.

(21) Appl. No.: 11/234,758

(22) Filed: Sep. 23, 2005

(65) Prior Publication Data

US 2006/0068513 A1 Mar. 30, 2006

(30) Foreign Application Priority Data

Sep. 27, 2004 (JP) ............................. 2004-280568

(51) Int. Cl.
*G01B 5/00* (2006.01)
*G06F 11/30* (2006.01)

(52) U.S. Cl. ..................... 702/33; 702/57; 702/183; 702/188; 438/18

(58) Field of Classification Search ............... 702/33, 702/34–38, 57–64, 182–189, 190; 324/765; 250/372; 356/601; 438/16
See application file for complete search history.

(56) References Cited

U.S. PATENT DOCUMENTS 6,642,066 B1 * 11/2003 Halliyal et al. ................ 438/16

FOREIGN PATENT DOCUMENTS

| JP | 2001-126324 A | | 5/2001 |
| JP | 2001126324 A | * | 5/2001 |
| JP | 2002-289614 A | | 10/2002 |
| JP | 2002289614 A | * | 10/2002 |
| JP | 2002289614 A | * | 10/2002 |
| JP | 2005126324 A | * | 5/2005 |

* cited by examiner

*Primary Examiner*—Edward Raymond
*Assistant Examiner*—Phuong Huynh
(74) *Attorney, Agent, or Firm*—Darby & Darby PC

(57) ABSTRACT

Among a plurality of parameters concerning a film forming condition, different parameter values are set for one parameter and the same predetermined values are set for other parameters to manufacture two pieces of film structures including a high-dielectric constant film or ferroelectric film formed on a substrate. The film characteristics of the respective film structures are analyzed by a spectroscopic ellipsometer, a film structure in which the ratio of the presence of an accompanying dielectric film is smaller, is determined to be good by comparing the analysis results, and a parameter value set for the manufacture of the good film structure is determined. Then similar processing is performed, to specify an optimal parameter value for one parameter, and similar processing is also performed for other parameters to specify an optimal parameter value for the other parameters.

20 Claims, 11 Drawing Sheets

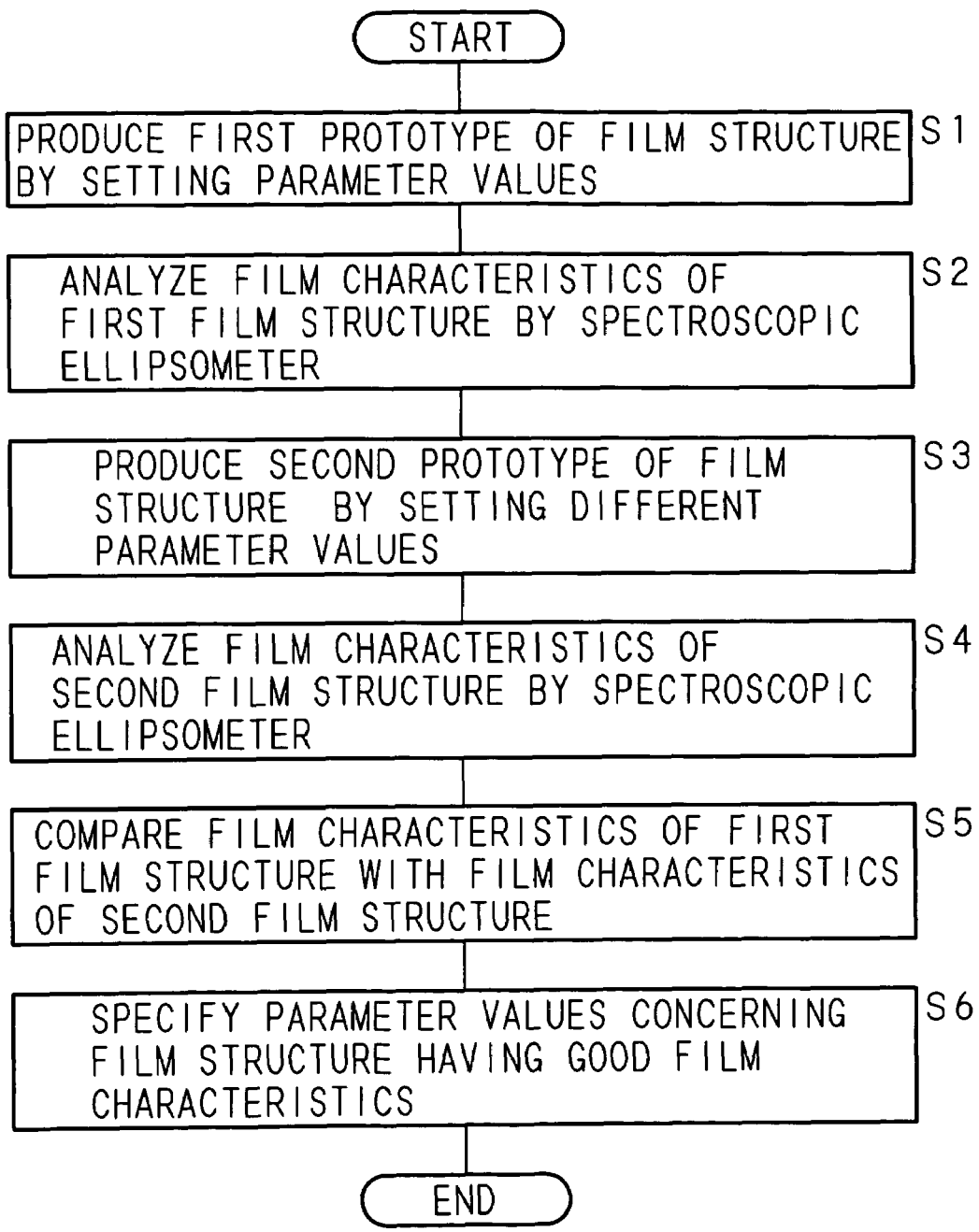

IDEAL PZT FILM STRUCTURE

ACTUAL PZT FILM STRUCTURE

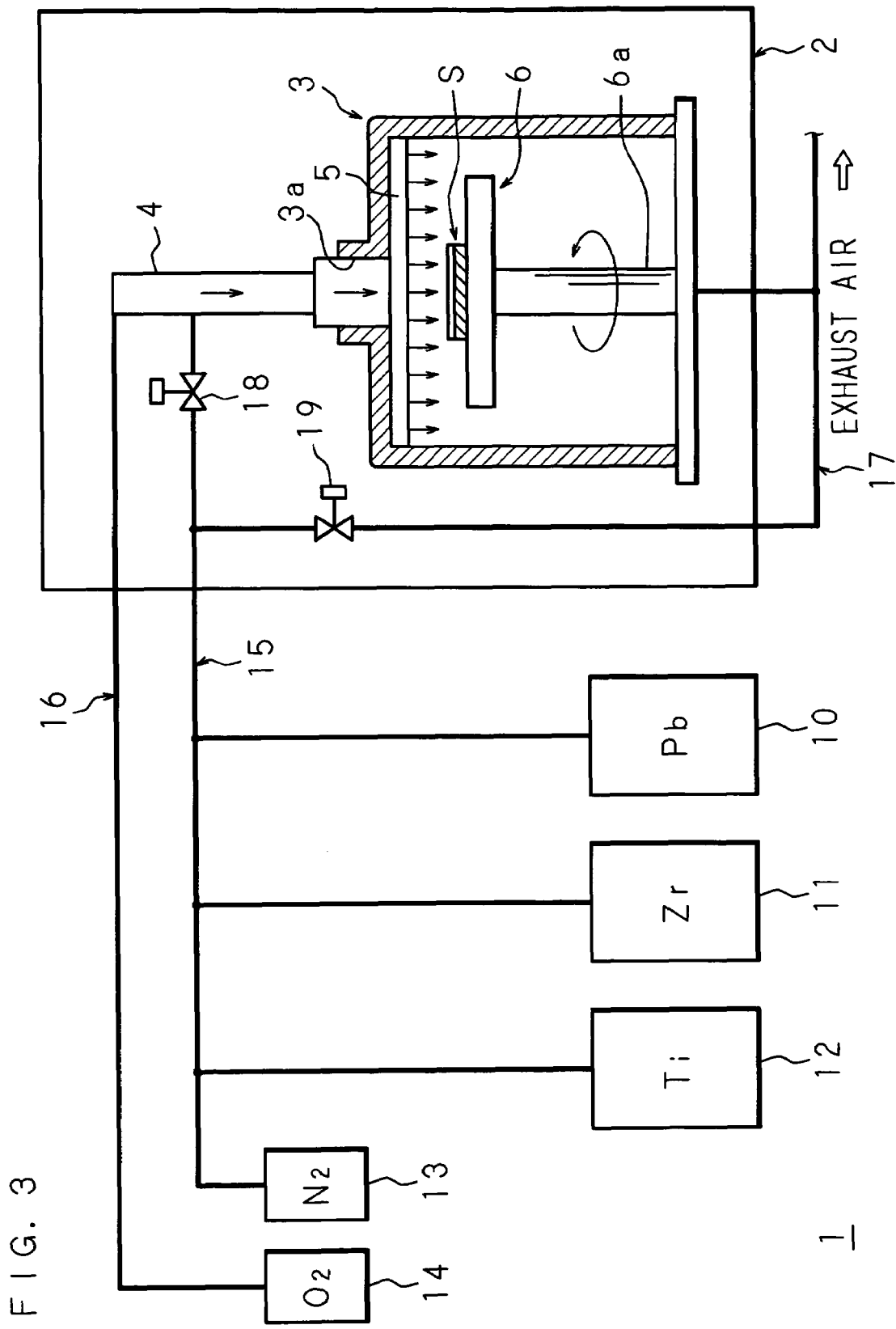

FILM FORMING CONDITION DETERMINATION METHOD, FILM FORMING METHOD, AND FILM STRUCTURE MANUFACTURING METHOD

CROSS-REFERENCE TO RELATED APPLICATION

This non-provisional application claims priority under 35 U.S.C. §119(a) on Patent Application No. 2004-280568 filed in Japan on Sep. 27, 2004, the entire contents of which are hereby incorporated by reference.

BACKGROUND OF THE INVENTION

1. Field of the Invention

The present invention relates to a film forming condition determination method capable of controlling the state of generation of an accompanying dielectric film that is generated with the formation of high-dielectric constant film or ferroelectric film, and efficiently determining an optimal film forming condition, for making the film structure closer to an intended film structure, relates to a film forming method capable of shifting smoothly a prototype of film structure to a mass-production stage, and further relates to a film structure manufacturing method capable of realizing an improvement in the yield, when mass-producing the film structure.

2. Description of Related Art

Conventionally, there are products produced using a film structure obtained by forming a high-dielectric constant thin film or ferroelectric thin film on a substrate, such as various kinds of semiconductor memory and semiconductor devices, and specific examples of these products include DRAM (Dynamic Random Access Memory), FRAM (Ferroelectric RAM), capacitor, piezoelectric elements such as an actuator, and electro-optic elements such as an optical shutter and an optical isolator.

For the film structure for use as a material for the above-mentioned various kinds of semiconductor products, first, the operation of finding a plurality of variables (parameters) concerning a film forming condition for manufacturing an intended film structure is performed, and then a prototype of the film structure is manufactured, based on the parameter values considered optimal. In order to examine whether the prototype has intended characteristics, in general, the prototype's evaluation is based on electrical measurement.

In order to electrically evaluate the prototype, first, an electrode part is formed on the prototype, then a required voltage is applied, by bringing a conducting probe into a contact with the formed electrode part (probing), or by wire bonding, and finally the capacitance (electric capacitance) of the dielectric film is measured to evaluate whether the prototype has intended characteristics. However, in order to evaluate the relationship between the film thickness and the dielectric constant from the measured capacitance, it is necessary to form, measure and compare a plurality of prototypes with different thickness. Note that the frequency band for electrical measurement of the dielectric constant ranges from about 100 kHz to about 5 GHz.

After confirming that a prototype has the intended characteristics, through the above-mentioned measurement and evaluation, products equal to the prototype should be manufactured in a factory, by a film forming apparatus, due to the shift from the prototype to a mass-production stage.

However, since a film forming apparatus for manufacturing the prototype and a film forming apparatus for mass-production in the factory differ in the scale, etc., even if the film forming conditions, optimized for the film forming apparatus for prototype are applied, as it is, to the film forming apparatus in the factory, products having the same characteristics as the prototype are rarely obtained. Therefore, a mass-production prototype is manufactured, by adjusting the film forming condition of the film forming apparatus in the factory, and then electrical measurement and evaluation of the manufactured mass-production prototype are done in the same manner as in the prototype stage, and the determination process of the optimal film forming conditions, for manufacturing a mass-production prototype having the same characteristics as the prototype, is performed.

After determining the optimal film forming conditions, those conditions are set for the film forming apparatus in the factory, and manufacture (mass-production) of film structure is performed. The manufacture of film structure includes a plurality of film forming steps, and the film structure is completed by performing the processing of the respective steps one after another. Moreover, electrical measurement is performed on the completed film structure as a part of a finished product inspection. It has been known that a transmission electron microscope (TEM) or a spectroscopic ellipsometer are used for the measurement of the film structure, as well as the above-mentioned electrical measurement.

The analysis performed using the spectroscopic ellipsometer is disclosed in Japanese Patent Applications Laid-Open No. 2002-289614 and No. 2001-126324. The Japanese Patent Application Laid-Open No. 2002-289614 discloses measuring the refractive index of a multi-layer film formed on the substrate entirely with a spectroscopic ellipsometer, and applying the measurement to the evaluation of the dielectric film, the temperature calibration and the manufacturing method. The Japanese Patent Application Laid-Open No. 2001-126324 discloses a method in which the variations in the film thickness and optical characteristic are evaluated by ellipsometer measurement in the course of the manufacture of an optical storage medium, and the manufacturing conditions are changed by feeding back the evaluation results to the manufacturing process. Note that the frequency band for the measurement of dielectric constant by the spectroscopic ellipsometer ranges from several hundred THz to about two thousand THz, and thus largely differs from the frequency band for the electrical measurement.

The above-described conventional electrical measurement has the problem that it takes a lot of time and work. In other words, in order to perform the measurement, first a plurality of film structures to be measured are prepared, and then probing or wire bonding is performed, after creating an electrode part for each film structure, and thus a lot of time and work are required. Note that if the electrode part is once formed on the film structure, the electrode part can never be removed, and therefore it is difficult to effectively use the film structure used for the measurement. Moreover, determining an optimal film forming condition, by evaluating a plurality of measurement results, creates a heavy labor burden, and particularly if the number of kinds of parameters concerning the film forming condition of a film structure to be manufactured is large, the same number of electrical measurements and the evaluation process are required for each kind, and consequently the labor burden increases.

Further, when determining an optimal film forming conditions in order to shift to the mass-production stage in the factory, it is also necessary to perform measurements and evaluation. However, since the number of objects to be measured and evaluated at the mass-production stage is much larger compared to the prototype stage, there is the problem that a lot of time and work are necessary to shift to the mass-production stage as well.

Furthermore, after shifting to the mass-production stage, it is physically impossible to form an electrode part after deposition of each intermediate film structure, and perform electrical measurement by probing or wire bonding, therefore, presently, a product inspection is performed on a finished film structure, obtained through a plurality of film forming steps. Thus, since an intermediate film structure, that may contain a defective layer, during any step of a film forming process, flows to the final film forming step, and as a result, a lot of steps are performed wastefully, an improvement of the yield is not achieved.

Since the methods of Japanese Patent Applications Laid-Open No. 2002-289614 and No. 2001-126324 do not take into account the shift to the mass-production stage and an improvement of the yield at the mass-production stage, even if the methods disclosed in Japanese Patent Applications Laid-Open No. 2002-289614 and No. 2001-126324 are applied, the above-mentioned problems cannot be solved. Moreover, the measurement and analysis by a transmission electron microscope (TEM) require even more work, compared with electrical measurement, and the degree of difficulty of the measurement is high. Therefore, even if the transmission electron microscope (TEM) is used, the above-mentioned problem cannot be solved.

On the other hand, in recent years, it was reported that when a high-dielectric constant film or ferroelectric film, whose electrically measured dielectric constant is not lower than 50, is formed on a substrate, an unknown accompanying film having dielectric characteristic is naturally formed following the formation of the high-dielectric constant film or ferroelectric film. This accompanying film may be formed at the interface between the high-dielectric constant film or ferroelectric film and the substrate, on the surface of the high-dielectric constant film or ferroelectric film, or both the interface and the film surface. Moreover, it has been found that when the high-dielectric constant film or ferroelectric film is a multi-layer structure, it may be formed at the interface between the respective films.

Although the presence of such an accompanying film is detected by electrical measurement, the single electrical measurement can not determine the characteristic of the accompanying film and the characteristic of the high-dielectric constant film or ferroelectric film separately. Besides, it is presumable, that the dielectric constant of the accompanying film may become higher or lower compared with the dielectric constant of the high-dielectric constant film or ferroelectric film under some film forming condition. However, it has not yet been established, how the dielectric constant of the accompanying film varies with a change in the film forming conditions, and there is a possibility, that the accompanying film may loose the characteristic of the high-dielectric constant substance or ferroelectric substance, when the dielectric constant of the accompanying film is low. Note that since the refractive index establishes a relationship similar to the dielectric constant, therefore the above discussion is also applied to the refractive index of the accompanying film.

Since the presence of the accompanying film prevents the film structure from having an intended characteristic, it is important to reduce the accompanying film and even more important to find a film forming conditions to eliminate the accompanying film. On the other hand, from a different point of view, it is expected to appreciate the importance of the capability to find a film forming conditions, capable of forming an intended film structure, including an accompanying film, by generating the accompanying film intentionally.

However, even when the methods of Japanese Patent Applications Laid-Open No. 2002-289614 and No. 2001-126324 are used, it is impossible to determine a film forming conditions capable of controlling the generation of the accompanying film.

BRIEF SUMMARY OF THE INVENTION

The present invention has been made with the aim of solving the above problem, and it is an object of the present invention to provide a film forming condition determination method capable of determining a film forming condition, that can control an accompanying film which is formed following the formation of a high-dielectric constant film or ferroelectric film on a substrate.

Another object of the invention is to provide a film forming method capable of significantly reducing the time and the work required to shift a film structure from a prototype stage to a mass-production stage.

A further object of the invention is to provide a film structure manufacturing method, capable of realizing the yield improvement at the mass-production level.

In order to solve the above problem, a film forming condition determination method, according to a first aspect, is characterized by comprising the steps of: forming a dielectric film, whose dielectric constant based on electrical measurement is not lower than 50, on a substrate by setting a predetermined value for a film forming condition variable; analyzing a characteristic of the formed film by a spectroscopic ellipsometer; comparing an analysis result with a reference characteristic value; determining from a comparison result whether or not to change the film forming condition variable; and determining a film forming condition by specifying a film forming condition variable based on a determination result.

In the first aspect, since the film characteristic of a high-dielectric constant film or ferroelectric film and that of an unknown accompanying dielectric film are separately analyzed, by performing analysis with the spectroscopic ellipsometer, it is possible to compare the analyzed characteristics of the respective films with a reference characteristic value, and if the characteristics of the respective films deviate from the reference characteristic value by comparison, it is possible to certainly determine that it is necessary to change the value set for the film forming condition variable. Therefore, compared with evaluation based on electric measurement that can analyze a multi-layer film only as a whole, the analysis accuracy can be significantly improved, and this method can be used to specify an appropriate film forming condition. Note that the reference characteristic value compared with the analysis result is a value about a film characteristic determined based on intended specification values, the past measurement values, and values obtained by calculation or the like.

A film forming condition determination method according to a second aspect is characterized by comprising: a first step of forming a dielectric film, whose dielectric constant based on electrical measurement is not lower than 50, on a substrate by setting a predetermined value for a film forming condition variable; a second step of analyzing a characteristic of the film formed in the first step by a spectroscopic ellipsometer; a third step of forming a dielectric film, whose dielectric constant based on electrical measurement is not lower than 50, on a substrate by setting a value different from the predetermined value set in the first step for the film forming condition variable; a fourth step of analyzing a characteristic of the film formed in the third step by the spectroscopic ellipsometer; and a fifth step of specifying a value of the film forming condition variable, based on a comparison between an analysis result in the second step and an analysis result in the fourth step.

In the second aspect, the film characteristic of a high-dielectric constant film or ferroelectric film and that of an unknown accompanying dielectric film are separately analyzed, by performing analysis with the spectroscopic ellipsometer, and the characteristics of films formed under different film forming conditions are respectively compared. It is therefore possible to determine easily a film, in which the presence of the accompanying dielectric film is smaller. As a result, when determining a film forming condition, that makes the presence of the accompanying dielectric film smaller, it is possible to determine certainly, whether to increase or decrease the value of the film forming condition variable, it is also possible to guess easily, how the value of optimal film forming condition variable should be changed, thereby improving the efficiency of work, concerning the specification of value of the film forming condition variable.

Regarding the contents of specifying a value of the film forming condition variable, based on the comparison between the respective analysis results, there may be a method in which a value of the film forming condition variable is specified, by individually comparing either the characteristic of the accompanying dielectric film or the characteristic of the dielectric film (high-dielectric constant film or ferroelectric film); and a method in which a value of the film forming condition variable is specified by taking into account the characteristics of both of the films. The contents of the former method may include, for example, determining which of the accompanying dielectric films in film structures formed under different film forming conditions has a characteristic closer to the reference characteristic value, and specifying a value corresponding to the formation of film structure having the closer characteristic for the value of the film forming condition variable; comparing the characteristics of the accompanying dielectric films to each other, without using the reference characteristic value, and specifying a value corresponding to the formation of the film structure having better film characteristic for the value of the film forming condition variable; determining which of the dielectric films has a characteristic closer to the reference characteristic value, and specifying a value corresponding to the formation of the dielectric film having closer characteristic for the value of the film forming condition variable; comparing the characteristics (for example, the film thickness) of the dielectric films to each other, and specifying a value corresponding to the formation of the film structure, having better film characteristic (for example, thicker film thickness), for the value of the film forming condition variable, etc. Moreover, when taking into account the characteristics of the both films, the comparison between the accompanying dielectric films and the comparison between the dielectric films are combined, and a value corresponding to better results in both comparisons, is set for the value of the film forming condition variable.

A film forming condition determination method according to a third aspect is characterized by that in the second step and the fourth step, a film thickness of an accompanying dielectric film, formed on one side or both sides of the dielectric film, following the formation of the dielectric film, is analyzed and obtained by the spectroscopic ellipsometer, and in the fifth step, the obtained film thicknesses of the respective accompanying dielectric films are compared, and a value corresponding to the formation of accompanying dielectric film having a thinner film thickness is specified as a value of the film forming condition variable.

In the third aspect, since a film structure including an accompanying dielectric film with thinner film thickness is determined to be good, based on the film thickness, that is one of the characteristics of the accompanying dielectric films, individually analyzed by the spectroscopic ellipsometer, the determination criteria for specifying a film forming condition variable is clear, and a film forming condition variable for decreasing the ratio of the accompanying dielectric film included in the film structure can be easily specified. As the location, where the accompanying dielectric film is generated, the accompanying dielectric film may be generated at the interface, with respect to the substrate or a film surface corresponding to one side of the dielectric film, or both the interface and film surface corresponding to both sides of the dielectric film.

A film forming condition determination method according to a fourth aspect is characterized by that in the first step, a plurality of dielectric films are formed as layers on the substrate, in each of the second step and the fourth step, a film thickness of an accompanying dielectric film, formed between the respective dielectric films following the formation of the dielectric films, is analyzed and obtained by the spectroscopic ellipsometer, and in the fifth step, the obtained film thicknesses of the respective accompanying dielectric films are compared, and a value corresponding to the formation of accompanying dielectric film, having thinner film thickness, is specified as a value of the film forming condition variable.

In the fourth aspect, by taking into account that an accompanying dielectric film is generated between films, when forming multi-layer dielectric films and comparing the film thickness of accompanying dielectric film between the films, it is possible to specify an appropriate value for the film forming condition variable to decrease the ratio of the accompanying dielectric film between the films.

A film forming condition determination method according to a fifth aspect is characterized by comprising the steps of: forming a dielectric film, whose dielectric constant based on electrical measurement is not lower than 50, on a substrate by setting a predetermined value for a film forming condition variable; analyzing and obtaining a refractive index of an accompanying dielectric film, formed on one side or both sides of the dielectric film, following the formation of the dielectric film, by a spectroscopic ellipsometer; comparing the obtained refractive index of the accompanying dielectric film and a refractive index of the dielectric film; determining from a comparison result, whether or not to change the film forming condition variable; and determining a film forming condition by specifying a film forming condition variable based on a determination result.

In the fifth aspect, since a determination is made as to whether or not to change the film forming condition variable, by comparing the refractive index of the accompanying dielectric film, obtained by analysis with the spectroscopic ellipsometer and the refractive index of the dielectric film, it is possible to manufacture an intended film structure, including the presence of the accompanying dielectric film, based on the numerical value of the refractive index. For example, when an accompanying dielectric film, having a refractive index lower than the refractive index of the dielectric film, is intentionally formed on one side or both sides of the dielectric film, it is possible to enclose and propagate the light, incident on the dielectric film of the film structure, by reflecting the light by the accompanying dielectric films, thereby contributing to the specification of a film forming condition variable, suitable for forming a film structure capable of using the dielectric film as a light wave guide. Moreover, if the electro-optic effect, etc. is also used, it is possible to control the propagating direction of light propagating in the dielectric film of the formed film structure.

A film forming condition determination method according to a sixth aspect is characterized by comprising: a first step of forming a dielectric film, whose dielectric constant based on electrical measurement is not lower than 50, on a substrate, by setting a predetermined value for a film forming condition variable, and stacking a film, whose refractive index is smaller than the dielectric film; a second step of analyzing and obtaining a refractive index of an accompanying dielectric film, formed at the interface on the substrate side, following the formation of the dielectric film in the first step, by a spectroscopic ellipsometer; a third step of forming a dielectric film, whose dielectric constant based on electrical measurement is not lower than 50, on a substrate, and stacking a film whose refractive index is smaller than the dielectric film on the dielectric film, by setting a value different from the predetermined value set in the first step for the film forming condition variable; a fourth step of analyzing and obtaining a refractive index of an accompanying dielectric film, formed at the interface on the substrate side, following the formation of the dielectric film in the third step, by the spectroscopic ellipsometer; and a fifth step of specifying a value of the film forming condition variable by comparing the refractive index of the accompanying dielectric film obtained in the second step and the refractive index of the accompanying dielectric film obtained in the fourth step.

In the sixth aspect, since a value of the film forming condition variable is specified, by comparing the refractive indices of the accompanying dielectric films generated at the interface on the substrate side of dielectric film of multi-layer film structure formed under different film forming conditions, it is possible to control easily the accompanying dielectric film to be generated. In other words, since the accompanying dielectric film is sometimes generated at the interface on the substrate side, in relation to some distortion between the dielectric film and the substrate, if the intended accompanying dielectric film is caused to be generated only at the interface on the substrate side, it is possible to reduce the items to be taken into account for specifying a film forming condition variable, and thus it is possible to specify efficiently and easily a film forming condition variable. Note that since a stacked film with a refractive index smaller than that of the dielectric film is formed on the top side of the dielectric film, the dielectric film of the finished film structure is sandwiched between the accompanying dielectric film and the stacked film with small refractive index, and therefore it is possible to obtain a film structure capable of using the dielectric film as a light wave guide.

A film forming method according to a seventh aspect of the invention is characterized by comprising: a first step of forming a film by a first film forming apparatus, by setting a predetermined value for a film forming condition variable in the first film forming apparatus; a second step of analyzing a characteristic of the film formed in the first step; a third step of forming a film by a second film forming apparatus by setting a value corresponding to the predetermined value set in the first film forming apparatus for a film forming condition variable in the second film forming apparatus; a fourth step of analyzing a characteristic of the film formed in the third step by a spectroscopic ellipsometer; a fifth step of comparing an analysis result in the second step and an analysis result in the fourth step; if it is found by the comparison in the fifth step, that the analysis results differ, a sixth step of specifying a value of the film forming condition variable to be set in the second film forming apparatus so that the analysis result in the fourth step becomes closer to the analysis result in the second step; and a seventh step of forming a film by the second film forming apparatus by setting the value specified in the sixth step for the film forming condition variable in the second film forming apparatus.

In the seventh aspect, when shifting from the prototype stage to the mass-production stage, by adjusting the film forming condition variable, corresponding to the second film forming apparatus to be used in the mass-production stage, so that the result of the analysis, made by the spectroscopic ellipsometer, becomes closer to that in the prototype stage, by this way it becomes possible to reduce the labor and burden concerning the analysis, compared with the analysis based on electrical measurement, and it is also possible to reduce the produced number of mass-production prototypes and therefore shift easily to the mass-production stage.

A film forming method according to an eighth aspect is characterized by that the first film forming apparatus and the second film forming apparatus perform film formation, by forming a dielectric film whose dielectric constant based on electrical measurement is not lower than 50, on the substrate.

In the eighth aspect, by performing analysis with the spectroscopic ellipsometer when mass-producing a high-dielectric constant film or ferroelectric film, it is possible to individually analyze the characteristic of the accompanying dielectric film that cannot be analyzed by electrical measurement, and therefore this method can be suitably used for the formation of PZT film structure used as the material for FRAM, etc.

A film forming method according to a ninth aspect is characterized by that in the sixth step, a value of the film forming condition variable is specified using the film forming condition determination method.

In the ninth aspect, by using the above-mentioned film forming condition determination method, to specify a film forming condition variable, it is possible to specify efficiently a film forming condition variable that can make the film characteristic of a film structure, formed by the second film forming apparatus, closer to the film characteristic of the film structure, formed by the first film forming apparatus, thereby contributing to the smooth shift to the mass-production stage.

A film structure manufacturing method, according to a tenth aspect, is a film structure manufacturing method for manufacturing a film structure, by performing processes in a plurality of film forming steps one after another, and characterized by comprising the steps of analyzing a characteristic of an intermediate film structure, processed in each film forming step, by a spectroscopic ellipsometer; determining whether or not the analyzed characteristic is within a reference characteristic range, corresponding to each intermediate film structure; and processing the intermediate film structure, determined to have a characteristic within the reference characteristic range, in the next film forming step.

In the tenth aspect, in order to continue to manufacture the film structure, while maintaining good quality after starting the mass-production of the film structure, the film characteristic of an intermediate film structure is analyzed by a spectroscopic ellipsometer in each film forming step, and the next film forming process is performed on the one with analysis result within the reference characteristic range. It is therefore possible to exclude an intermediate film structure, determined to be defective in the course of the process and continue to perform the film forming process only on good products, thereby achieving an improvement in the yield of finished product.

A film structure manufacturing method according to an eleventh aspect is characterized by that the film structure is constructed by forming a dielectric film, whose dielectric constant based on electrical measurement is not lower than 50, on a substrate.

In the eleventh aspect, by performing analysis with the spectroscopic ellipsometer, when managing the quality of mass-production of a so-called high-dielectric constant film or ferroelectric film, it is possible to analyze the characteristic of the accompanying dielectric film that cannot be individually analyzed by electrical measurement, and therefore this method can be suitably used for the formation of PZT film used as the material for FRAM, etc.

In the first aspect, by performing analysis with the spectroscopic ellipsometer, it is possible to analyze separately the film characteristics of a high-dielectric constant film or ferroelectric film and an accompanying dielectric film, and it is possible to significantly improve the analysis accuracy compared with evaluation based on a conventional electrical measurement, thereby contributing to the specification of appropriate film forming condition variable.

In the second aspect, the film characteristic of a high-dielectric constant film or ferroelectric film and that of an accompanying dielectric film are analyzed separately, by performing analysis with the spectroscopic ellipsometer, and the characteristics of films formed under different film forming conditions are respectively compared. Therefore, it is possible to determine easily a film in which the presence of the accompanying dielectric film is smaller, and it is possible to find out easily how the value of the film forming condition variable should be changed, thereby improving the efficiency of work concerning the specification of a value of the film forming condition variable.

In the third aspect, based on film thickness, that is one of the characteristics of the accompanying dielectric films, analyzed and obtained separately by the spectroscopic ellipsometer, a film structure including an accompanying dielectric film with a thinner film thickness is determined to be good. Therefore, the determination criteria for specifying a film forming condition variable is clear, and a film forming condition variable for reducing or eliminating the accompanying dielectric film can be specified easily.

In the fourth aspect, when a multi-layer film of dielectric is formed, an appropriate value of the film forming condition variable, to decrease the ratio of the accompanying dielectric film between films can be specified, by comparing the film thickness of accompanying dielectric film between the films.

In the fifth aspect, since a determination as to whether or not to change the film forming condition variable is made, by comparing the refractive index of the accompanying dielectric film obtained by analysis with the spectroscopic ellipsometer and the refractive index of the dielectric film, it is possible to easily specify a film forming condition variable for generating an intended accompanying dielectric film based on the numerical value of refractive index.

In the sixth aspect, since the refractive indices of the accompanying dielectric films generated at the interface on the substrate side of dielectric films in a multi-layer film structure formed under different film forming conditions are respectively compared, it is possible to control more easily the generation of accompanying dielectric film.

In the seventh aspect, by adjusting the film forming condition variable, corresponding to the second film forming apparatus, to be used in the mass-production stage, so that the result of analysis performed by the spectroscopic ellipsometer becomes closer to that in the prototype stage, by this way it becomes possible to reduce the labor and burden concerning the analysis, compared to the analysis based on electrical measurement, and it is also possible to reduce the produced number of mass-production prototypes and therefore shift easily to the mass-production stage.

In the eighth aspect, by performing analysis with the spectroscopic ellipsometer, when mass-producing a high-dielectric constant film or ferroelectric film, it is possible to individually analyze the characteristic of an accompanying dielectric film itself that cannot be analyzed by electrical measurement, and it becomes possible to shift to the mass-production stage by setting an optimal film forming condition for mass-production.

In the ninth aspect, by using the above-mentioned film forming condition determination method to specify a film forming condition variable, it is possible to specify efficiently a film forming condition variable that can make the film characteristic of a film structure, formed by the second film forming apparatus closer to the film characteristic of the film structure, formed by the first film forming apparatus, and it is therefore possible to shift smoothly to the mass-production stage.

In the tenth aspect, the film characteristic of an intermediate film structure is analyzed by the spectroscopic ellipsometer in each film forming step, and the next film forming process is performed on the previous one with analysis result within the reference characteristic range. It is therefore possible to exclude an intermediate film structure determined to be defective in the course of the process and continue to perform the film forming process only on good products, thereby achieving an improvement in the yield of the finished product.

In the eleventh aspect, by performing analysis with the spectroscopic ellipsometer, when managing the quality of mass-production of a so-called high-dielectric constant film or ferroelectric film, it is possible to analyze the characteristic of an accompanying dielectric film itself, that cannot be analyzed by electrical measurement.

The above and further objects and features of the invention will more fully be apparent from the following detailed description with accompanying drawings.

BRIEF DESCRIPTION OF THE SEVERAL VIEWS OF THE DRAWINGS

FIG. 1 is a flowchart showing the processing steps of a film forming condition determination method according to the first embodiment of the present invention;

FIG. 3 is a schematic view showing the structure of a MOCVD apparatus;

DETAILED DESCRIPTION OF THE INVENTION

FIG. 1 is a flowchart showing the processing steps of a film forming condition determination method, according to the first embodiment of the present invention. The present invention is a method for determining a film forming condition, in forming a high-dielectric constant film or ferroelectric film as a dielectric film with a dielectric constant of not lower than 50, based on electrical measurement, on a substrate (for example, with a deposited material for electrode), and more particularly for determining a film forming condition, capable of forming a film structure, including an intended high-dielectric constant film or ferroelectric film, by reducing an accompanying dielectric film, that is generated at the interface between the substrate and the high-dielectric constant film or ferroelectric film, with the formation of the high-dielectric constant film or ferroelectric film.

Figure 2A:
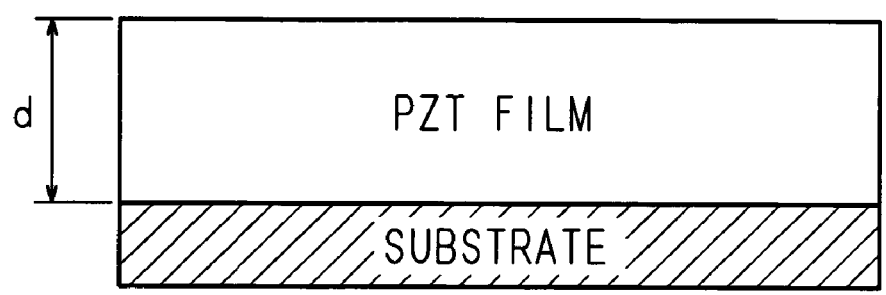
FIG. 2A is a schematic view showing the structure of an ideal PZT film structure.
Figure 2B:
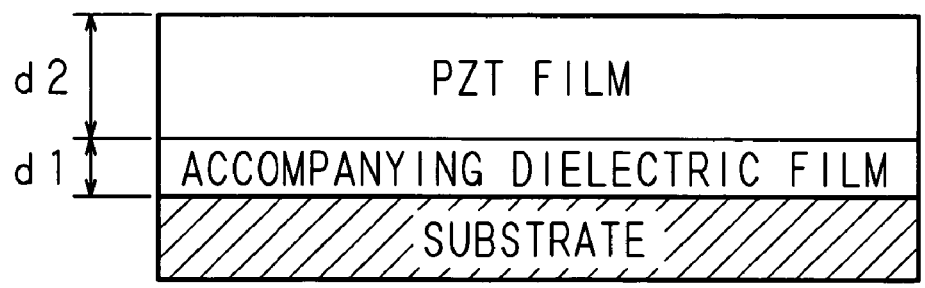
FIG. 2B is a schematic view showing the structure of an actual PZT film structure.

The first embodiment illustrates, as shown in FIG. 2A, the case where a single PZT (lead zirconate titanate) film, as a ferroelectric film, is formed in a stacked film with thickness d on a Si (silicon) substrate, having a Pt (platinum) film, deposited on a surface thereof When the PZT film is formed on the substrate, a multi-layer film structure is actually produced, as shown in FIG. 2B, because a layer of accompanying dielectric film is produced at the interface between the PZT film and the substrate. In this case, a dimension calculated by adding up a film thickness d2 of the PZT film and a film thickness d1 of the accompanying dielectric film is equal to the film thickness d of the PZT film in a PZT film structure, usually considered having a film structure (hereinafter referred to as the ideal PZT film structure) shown in FIG. 2A, and the sum of the inverse values of the electrostatic capacitance of the respective films in the actual PZT film structure shown in FIG. 2B is equal to the inverse value of the electrostatic capacitance of the PZT film in the ideal PZT film structure shown in FIG. 2A. Note that when the material of the accompanying dielectric film is taken into consideration, the accompanying dielectric film belongs to a kind of PZT film, and the PZT is indicated as ($PbZr_xTi_{1-x}O_3$).

FIG. 3 shows an outline of a MOCVD (Metal Organic CVD) apparatus 1 (cold wall type) as a film forming apparatus for a PZT film structure. The MOCVD apparatus 1 comprises a reaction chamber 3 inside a main body 2, and a first raw material tank 10, a second raw material tank 11 and a third raw material tank 12 that stores Pb (lead), Zr (zirconium), and Ti (titanium) as metal complex raw material in a liquid state by heating them with a heater. The respective raw material tanks 10 to 12 are connected to a cylindrical gas supply unit 4, projecting from the top of the reaction chamber 3, through a raw material pipe 15 with a valve 18 therebetween. Moreover, the MOCVD apparatus 1 has a nitrogen tank 13 and an oxygen tank 14 storing $N_2$ (nitrogen gas) and $O_3$ (oxygen gas). The nitrogen tank 13 is connected to the raw material pipe 15, and the oxygen tank 14 is connected to the gas supply unit 4 through an oxygen supply pipe 16. Although each of the raw material tanks 10 through 12 is provided with a valve for adjusting the flow rate, the illustration thereof is omitted.

Further, in the MOCVD apparatus 1, an opening 3a is formed in the top of the reaction chamber 3, to connect the gas supply unit 4 to the inside of the reaction chamber 3, and a shower plate 5 having many holes, formed equally to pass the gas is attached to the top surface in the chamber. The reaction chamber 3, is a structure capable of adjusting the internal pressure, has a mount base 6 incorporating a heater and retaining a substrate S inside the chamber, and allows a support shaft supporting the mount base 6 to rotate at several hundred rpm. A discharge pipe 17, for discharging the gas inside the chamber, is connected to the reaction chamber 3, and the discharge pipe 17 is also connected to the raw material pipe 15 through a valve 19.

An outline of manufacture of a PZT film structure using the MOCVD apparatus 1 having the above-described structure is as follows. The respective raw material gases vaporized in the raw material tanks 10 through 12, are guided to the gas supply unit 4 through the raw material pipe 15, passed through the shower plate 5, guided into the reaction chamber 3, where the pressure is increased, and vapor-deposited on the rotating substrate S, heated on the mount base 6 to form the PZT film. When forming a film by the MOCVD apparatus 1 in this manner, it is necessary to set a plurality of parameters (variables), concerning film forming conditions, such as the flow rate of the respective gases, the internal pressure of the reaction chamber 3, and the heating temperature of the substrate S, to the predetermined values (parameter values), and it is important to set an appropriate parameter value for each parameter, in order to form an ideal PZT film structure.

Figure 4:
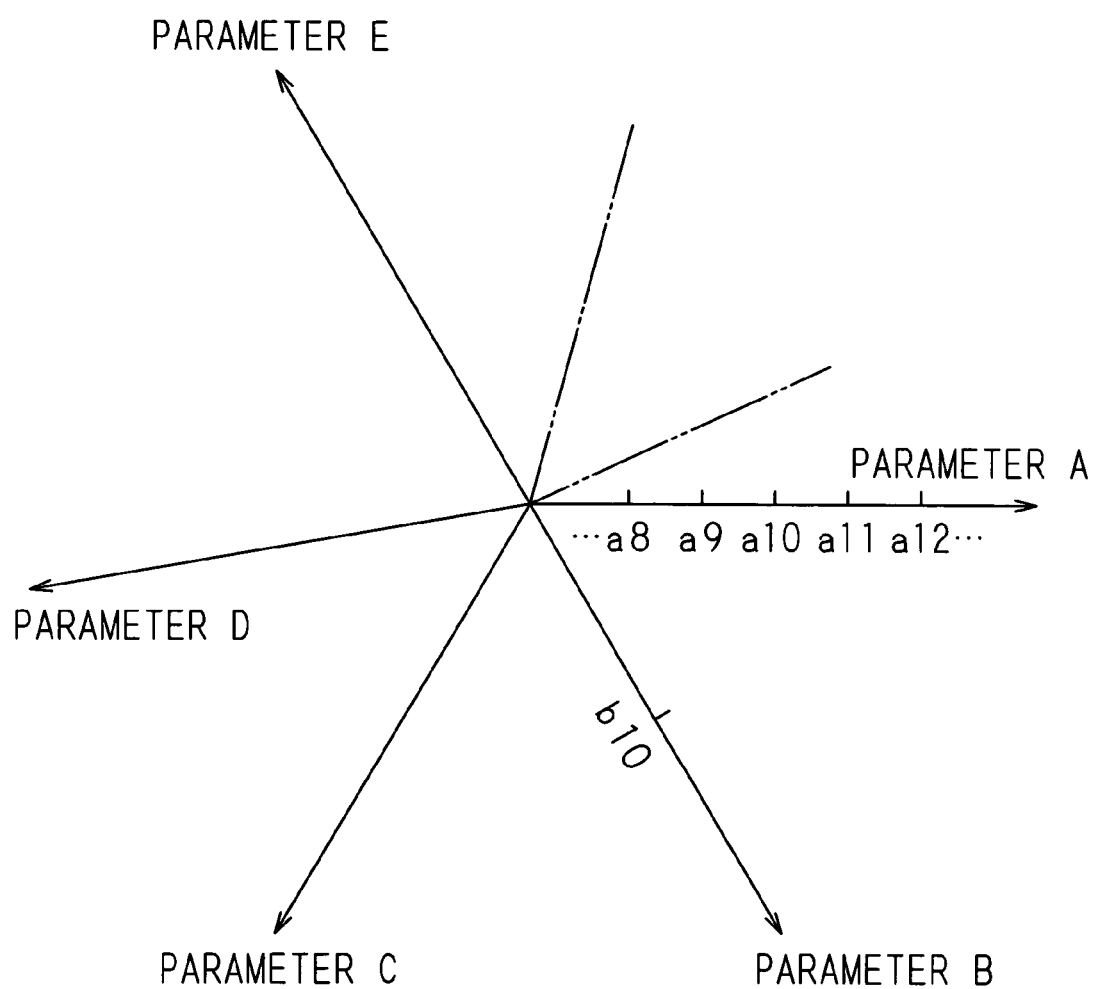
FIG. 4 is a view showing the relationship between the parameters concerning a film forming condition.

In order to set the parameter values of the respective parameters, the operation of specifying an appropriate parameter value for a multi-dimensional matrix shown in FIG. 4 needs to be performed. For example, if there are a plurality of parameters A, B, C and so on, as the parameters concerning film forming conditions, the flow rate of Pb gas corresponds to the parameter A in FIG. 4, and the flow rate of Zr gas, the flow rate of Ti gas, the pressure in the reaction chamber 3, and the heating temperature of the substrate S correspond to the parameter B, parameter C, parameter D, and parameter E, respectively.

It is necessary to specify appropriate parameter values for these parameters. However, in general, it is difficult to specify appropriate values for a plurality of parameters simultaneously, and therefore, in this embodiment, two pieces of PZT film structure are generated, by setting two different parameter values for one kind of parameter and setting the same parameter values for other parameters, and the multi-layer film of each of the two pieces of PZT film structure is analyzed. A PZT film structure, in which the presence of the accompanying dielectric film is smaller, as shown in FIG. 2B, is determined to be a good PZT film structure, and the parameter values concerning the formation of this good PZT film structure are selected.

For example, two pieces of PZT film structures are formed, by performing the film forming processes twice, by setting the same values for the parameters other than the parameter A, and setting a parameter value "a10" and a parameter value "a11 (a11>a10)" for the parameter A. The multi-layer film of each of the formed PZT film structures is analyzed, and if the PZT film structure formed based on "a10" is better, in terms of the existing probability of the accompanying dielectric film, the "a10" is first selected as the parameter value of the parameter A. Next, in order to specify a further optimal value, a PZT film structure is formed and analyzed, by setting a parameter value "a9 (a9<a10)" for the parameter A, and then compared with the PZT film structure corresponding to "a10". If the PZT film structure formed based on "a9" is better compared with the PZT film structure corresponding to "a10", in terms of the existing probability of the accompanying dielectric film, the "a9" is selected as the parameter value of the parameter A.

Then, the same processes as above are performed for "a8", etc. better than "a9" in the same manner, to specify an optimal parameter value for the parameter A. By performing such a specifying method, there is no need to form a PZT film structure for a value larger than "a11", and it is possible to reduce the number of prototypes to be manufactured and the number of times of the analysis to be performed, and it is possible to determine an optimal film forming condition, for forming an intended PZT film, without unnecessary operations. When the value of the parameter A is specified, a similar parameter value specifying process is performed on the other parameters B, C, etc. one after another, to specify optimal parameter values for all the parameters A, B, etc. and to form a PZT film structure with reduced or nonexistent accompanying dielectric film.

Note that when forming a high-dielectric constant film or ferroelectric film other than PZT on the substrate, or when film forming apparatuses, other than a MOCVD apparatus are used, the number and kinds of parameters may differ, and there may be a parameter whose value can not be set independently, as it may vary in correlation to other parameters. However, even when such various types of film forming apparatuses are used, an optimal parameter value could be specified within a possible range, in the same manner, as determining a film forming condition for a PZT film structure mentioned above. Note that examples of the film forming apparatuses, other than MOCVD include, a sputtering apparatus, a sol-gel processing apparatus, etc.

Moreover, in this embodiment, in order to specify optimal parameter values, electrical measurements are not performed for the analysis (evaluation) of the multi-layer film of the formed PZT film structure, but measurement and analysis are performed by a spectroscopic ellipsometer. Since the spectroscopic ellipsometer performs the measurement in a non-contact manner, there is no need to form an electrode part and perform probing or wire bonding, as in the case of electrical measurement, and it is possible to analyze the characteristics of the multi-layer film for each layer, by analyzing one sample. Therefore, if the analysis of the same content is performed, the spectroscopic ellipsometer can perform measurement and analysis within about one tenth of a time required for the electrical measurement. Thus, by specifying parameter values based on the analysis results of the spectroscopic ellipsometer, it is possible to specify efficiently optimal parameter values.

Figure 5:
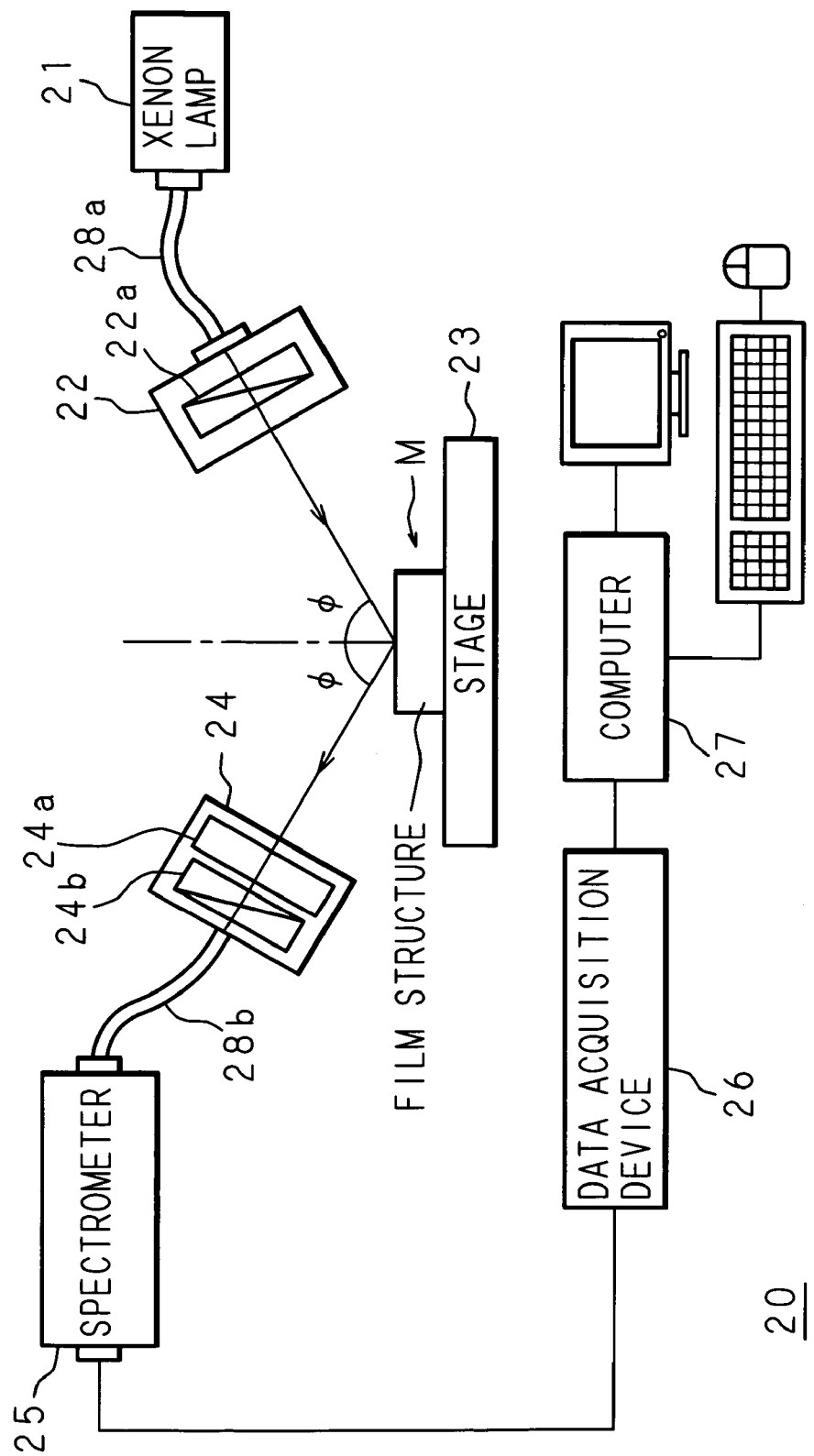
FIG. 5 is a schematic view showing the structure of a spectroscopic ellipsometer.

FIG. 5 is a schematic view showing the structure of a spectroscopic ellipsometer 20. The spectroscopic ellipsometer 20 analyzes the optical characteristic of each layer of a film structure (PZT film structure) M having a multi-layer film structure, by applying polarized light to the film structure M, and is constructed by connecting a xenon lamp 21 and a light polarizer 22 with a first optical fiber cable 28a, to apply polarized light to the film structure M, mounted on a stage 23 and receive reflected light (polarization state of light) from the film structure M by a light receiver 24. The light receiver 24 is connected to a spectrometer 25 through a second optical fiber cable 28b. The spectrometer 25 measures the light for each wavelength and transmits the measurement results as analog signals to a data acquisition device 26. The data acquisition device 26 converts the analog signals into predetermined values and transmits them to a computer 27, and then the computer 27 analyzes them.

Note that the xenon lamp 21 generates white light including a plurality of wavelength components as a light source, and the light polarizer 22 includes a polarizer 22a, therein for polarizing white light, to apply the polarized light to the film structure M at an incident angle φ. The light receiver 24 incorporates a PEM (Photo Elastic Modulator) 24a and an analyzer 24b therein, guides the light reflected from the film structure M to the analyzer 24b through the PEM 24a, and passes specific polarized light among various kinds of polarized light phase-modulated by the PEM 24a. Further, the spectrometer 25 makes a spectral separation of the light, received from the light receiver 24, measures the polarization state for each wavelength, and sends the results as analog signals to the data acquisition device 26.

The data acquisition device 26 calculates a phase difference Δ and an amplitude ratio Ψ of a polarization state (p-polarization, s-polarization) of measured reflected light at each wavelength, based on the signal transmitted from the spectrometer 25 and sends the calculation result to the computer 27. It should be noted that the phase difference Δ and the amplitude ratio Ψ have a relation of the following expression (1) with respect to a complex Fresnel reflection coefficient Rp of p-polarized light and a complex Fresnel reflection coefficient Rs of s-polarized light:

$$Rp/Rs = \tan \psi \cdot \exp(i \cdot \Delta) \quad (1)$$

Here, i is an imaginary unit (the same goes hereinafter). Rp/Rs is referred to as a ratio of the complex Fresnel reflection coefficients ρ.

The computer 27 analyzes the film structure M, based on the phase difference Δ and the amplitude ratio ψ of the polarization state obtained by the data acquisition device 26, and analyzes the optical characteristics of the PZT film structure shown in FIG. 2B, by determining for each layer: the refractive index, extinction coefficient and the film thickness of the PZT film and the accompanying dielectric film. More specifically, when the complex refractive indices of the ambient and the substrate are known, from the measured phase difference Δ and the amplitude ratio ψ, the computer 27 forms a model, corresponding to the material structure of the PZT film structure, and obtains the thickness and the complex refractive index of each film. When n represents the refractive index of the film to be analyzed and k represents the extinction coefficient, the complex refractive index N can be calculated from the following optical expression (2):

$$N = n - ik \quad (2)$$

Moreover, assuming that the wavelength of light to be irradiated by the light polarizer 22 is λ, the phase difference Δ and the amplitude ratio Ψ, calculated by the data acquisition device 26, have the relation of the following expression (3) to the film thickness d, of a film to be analyzed, the refractive index n and the extinction coefficient k.

$$(d, n, k) = F(\rho) = F(\psi(\lambda, \phi), \Delta(\lambda, \phi)) \quad (3)$$

It should be noted that the computer 27 performs a process (fitting) of changing the film thickness, parameters of the dispersion formula and the like, so that a difference between a model spectrum ($\Psi_M(\lambda_i)$, $\Delta_M(\lambda_i)$), obtained theoretically from the formed model, and a measured spectrum ($\Psi_E(\lambda_i)$, $\Delta_E(\lambda_i)$), related to the measurement result obtained by the data acquisition device 26, becomes minimal, using the film thickness of a film, to be analyzed, and a dispersion formula, which represents the wavelength dependence of the complex dielectric constant and includes a plurality of parameters. It should be noted that an example of the dispersion formula to be applied is represented by the following expression (4).

$$\varepsilon = \varepsilon_\infty + \frac{(\varepsilon_s - \varepsilon_\infty)\varpi_t^2}{\varpi_t^2 - \varpi^2 + i\Gamma_0\varpi} + \frac{\varpi p^2}{-\varpi^2 + i\Gamma_D\varpi} + \sum_{j=1}^{2} \frac{f_j\varpi_{oj}^2}{\varpi_{oj}^2 - \varpi^2 + i\gamma_j\varpi} \quad (4)$$

In the expression (4), $\in$ at the left-hand side denotes a complex dielectric constant, $\in_\infty$ and $\in_S$ denote dielectric constants, $\Gamma_0$, $\Gamma_D$ and $\gamma_j$ denote damping factors, and $\omega_{oj}$, $\omega_t$ and $\omega_P$ denote angular frequencies (oscillator frequency, transverse frequency, plasma frequency). It should be noted that $\in_\infty$ is a dielectric constant at high frequency (high frequency dielectric constant) and $\in_S$ is a dielectric constant at low frequency (static dielectric constant). Moreover, the complex dielectric constant $\in$ (corresponding to $\in(\lambda)$) and the complex refractive index N (corresponding to N($\lambda$)) have the relation of the following expression (5).

$$\in(\lambda) = N^2(\lambda) \quad (5)$$

To give a simplified explanation of the fitting, assuming that T measurement data pairs in a case of measurement of the film material M are Exp(i=1, 2, ..., T) and data pairs calculated from the model, are Mod(i=1, 2, ..., T), the mean square error $\lambda^2$, of the least squares method, using $\sigma_i$ as the standard deviation, is obtained by the following expression (6), since the measurement error is to be normally distributed. It should be noted that P is the number of parameters. When the value of the mean square error $\lambda^2$ is small, the matching between the measurement result and the formed model is good, and the minimal value of the mean square error $\lambda^2$, obtained by comparing a plurality of models, corresponds to the best model.

$$\chi^2 = [1/(2T - P)] = \sum_{i=1}^{T} (\text{Exp}_i - \text{Mod}_i)^2 / \sigma_i^2 \quad (6)$$

A sequence of steps of processes related to sample analysis, to be performed by the computer 27, described above, are defined in a computer program for sample analysis stored in the storage unit in the computer, and the computer 27 can analyze the characteristics of each film of the PZT and the accompanying dielectric film in the PZT film structure, by performing the above-mentioned analysis processes.

Figure 6:
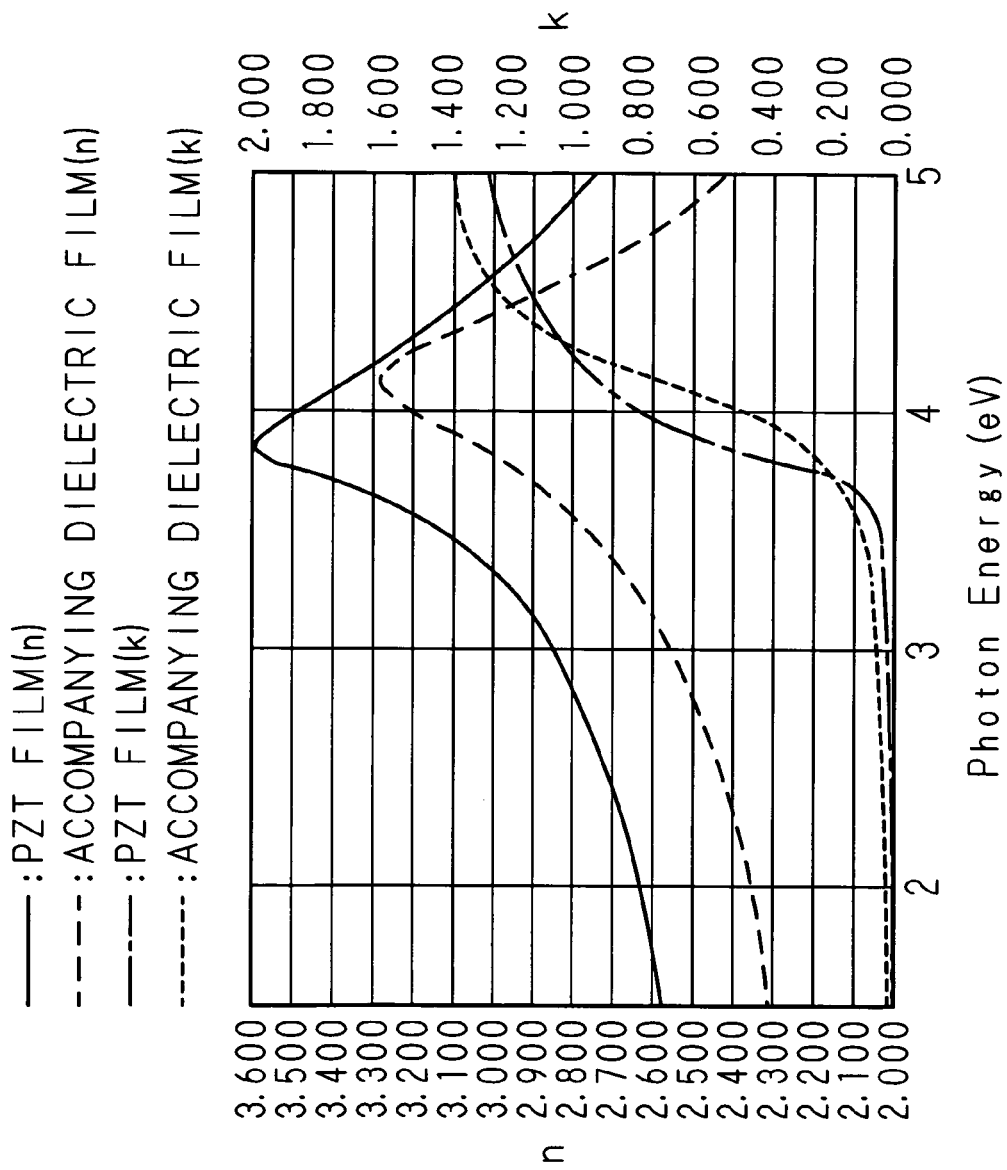
FIG. 6 is a graph showing one example of the analysis results of a multi-layer film in a PZT film structure by the spectroscopic ellipsometer.

The graph in FIG. 6 shows one example of the characterization results of analyzing the PZT film structure by the spectroscopic ellipsometer 20. The PZT film structure in this example includes a PZT film and an accompanying dielectric film formed following the formation of the PZT film. The material of the accompanying dielectric film is a PZT material, but the optical characteristic of the accompanying dielectric film differs from that of the intentionally formed PZT film. In other words, the extinction coefficient (k) of the PZT film suddenly rises, when the numerical value of photon energy exceeds 3.6 or so, while the extinction coefficient (k) of the accompanying dielectric film rises gradually and is shifted to the right side (the side where the numerical value of photon energy is larger), compared with the extinction coefficient (k) of the PZT film. This means that the ferroelectric characteristic of the accompanying dielectric film is inferior to the PZT film. Moreover, it was found, through the analysis by the spectroscopic ellipsometer 20, that the film thickness d2 of the PZT film structure was about 2612.37 (angstrom), and the film thickness d1 of the accompanying dielectric film was about 71.98 angstrom. Therefore, for the PZT film structure shown in FIG. 2B, it is possible to analyze separately the film thickness d1, of the accompanying dielectric film, and the film thickness d2, of the PZT film, by using the spectroscopic ellipsometer 20, and it is also possible to analyze the characteristics such as the refractive index and the extinction coefficient for each film. It is thus possible to evaluate whether or not the formed PZT film has the intended characteristics.

Note that the characteristics of the accompanying dielectric film included in the PZT film structure, shown in the graph of FIG. 6, are merely one example, and the actual characteristics of the accompanying dielectric film may vary. For example, the accompanying dielectric film may have a higher dielectric constant compared with the PZT film, or may have lost the ferroelectric characteristic due to a decrease in the dielectric constant.

The film forming condition determination method according to the present invention, that performs the above-described processes, will be clarified based on the flowchart of FIG. 1. First, a first prototype of film structure (PZT film structure) is produced by setting predetermined parameter values for parameters of a film forming condition (for example, setting "a10" for the parameter A shown in FIG. 4 and predetermined values for other parameters) (S1). Next, the film characteristics (film thickness, dielectric constant, etc.) of the first film structure are analyzed by the spectroscopic ellipsometer 20 (S2).

On the other hand, a second prototype of film structure (PZT film structure) is produced, by setting parameter values different from the parameter values, concerning the formation of the first film structure (for example, setting "a11" for the parameter A shown in FIG. 4 and the same predetermined values for other parameters) (S3), and the film characteristics (film thickness, dielectric constant, etc.) of the second film structure are analyzed by the spectroscopic ellipsometer 20 (S4).

Then, the analyzed film characteristics of the first film structure and the film characteristics of the second film structure are compared (S5). In this comparison, the value of the film thickness d1, of the accompanying dielectric film, and the film characteristic of the PZT film (whether the dielectric constant has an intended numerical value), etc. are evaluated. Finally, a film structure, which has thinner film thickness d1, of the accompanying dielectric film, and has the film characteristic of the PZT film closer to the intended numerical value is determined to have good film characteristic, and the parameter values for the film structure having the good film characteristic are specified (selected) (S6). In the comparison of film characteristics, it could be also possible to compare other analyzed characteristics (such as the refractive index and extinction coefficient) as well as the film thickness.

Then, an optimal parameter value for one parameter is finally specified, by performing the above-described film forming condition determination method on one parameter after another, and optimal parameter values are further specified for all other parameters, by performing similar processing on the other parameters, and consequently a film forming condition, for forming a film structure close to the ideal PZT film structure, shown in FIG. 2A, is finally determined.

For the determination as to whether or not the film structure has good film characteristics, a determination may be made that accompanying dielectric film with a thinner film thickness d1 has good film characteristic, based only on the film thickness d1 as the characteristic of the accompanying dielectric film, or a determination may be made that the PZT film with a thicker film thickness d2 and a film characteristic (such as a dielectric constant) closer to the intended value has good film characteristic, based on the film thickness d2 and the film characteristic as the characteristics of the PZT film. Further, the film forming condition determination method according to Embodiment 1 may also be applied to determine a film forming condition of high dielectric or ferroelectric other than PZT, and may also be applied, for example, to form a PLZT film.

Figure 7A:
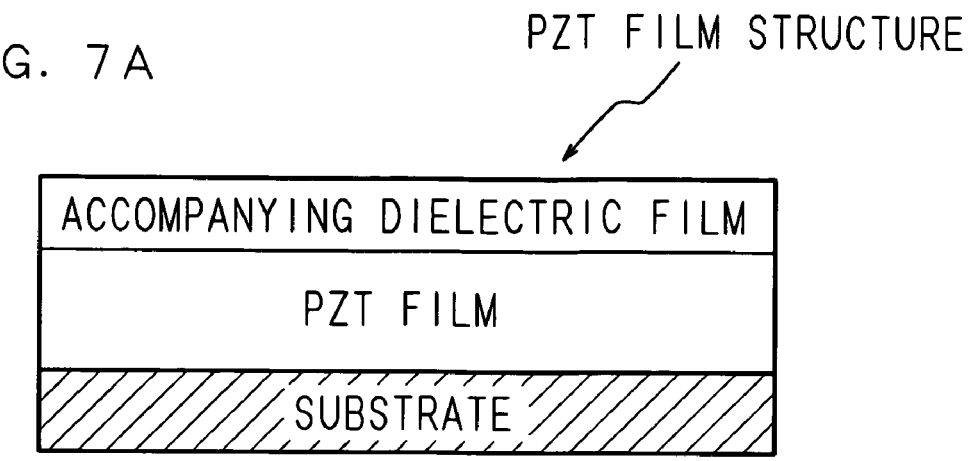
FIG. 7A is a schematic view of a PZT film structure with an accompanying dielectric film formed on a film surface.
Figure 7B:
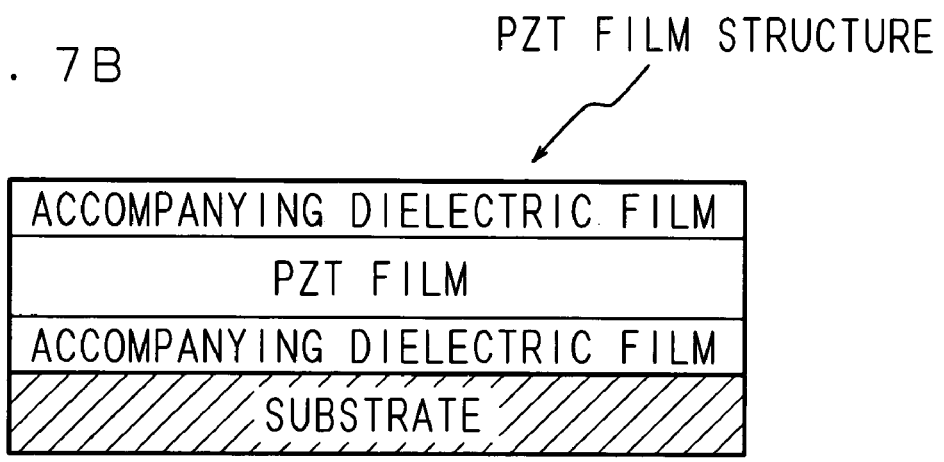
FIG. 7B is a schematic view of a PZT film structure with accompanying dielectric films formed to sandwich a PZT film.
Figure 7C:
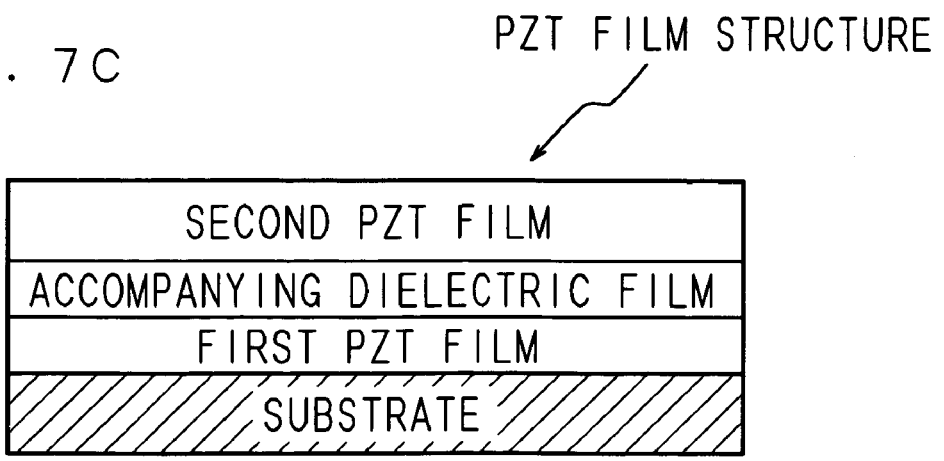
FIG. 7C is a schematic view of a PZT film structure with an accompanying dielectric film formed between two layers of PZT films.

Although the determination of the film forming condition was explained with the respect to the accompanying dielectric film, generated at the interface between the PZT film and the substrate, as shown in FIG. 2B, the film forming condition may be determined in the same manner, with respect to an accompanying dielectric film generated on the surface of the PZT film, as shown in FIG. 7A, and the accompanying dielectric films, generated on the both sides of the film, on the substrate side and the film surface of the PZT film, as shown in FIG. 7B. Moreover, the determination of the film forming condition may also be applied to an accompanying dielectric film, generated between PZT films of a PZT film structure, formed by stacking between the first PZT film and second PZT film, on the substrate, as shown in FIG. 7C.

Further, when determining whether or not to change the parameter value, temporarily set at present, it may be possible to perform the processing, concerning the film forming condition, by comparison with reference values. found in advance, instead of forming two pieces of film structures under different film forming conditions. More specifically, it is also possible to apply a method (film forming condition determination method) in which the film characteristics of a film structure obtained by forming a high-dielectric constant film or ferroelectric film, on a substrate, by setting predetermined parameter values is analyzed by a spectroscopic ellipsometer; the analyzed results are compared with reference characteristic values derived from prototype values, design values, etc.; and if it is found from the comparison result, that the analyzed value exceeds an allowed range, based on the reference characteristic value, a determination is made that there is a need to change the set parameter value, whereas if the analyzed value is within the allowed range, a determination is made that there is no need to change the parameter value. With the use of such a method, it is also possible to easily determine, whether or not a parameter value is appropriate.

On the other hand, in the contrary to the process to find a film forming condition capable of reducing or eliminating the accompanying dielectric film, the above-described film forming condition determination method is applicable to intentionally generate an accompanying dielectric film having intended characteristics. Note that a film structure including a high-dielectric constant film or ferroelectric film, on which an accompanying dielectric film is intentionally formed, is suitable as a material for an optical waveguide, with specific reflection properties.

Figure 8A:
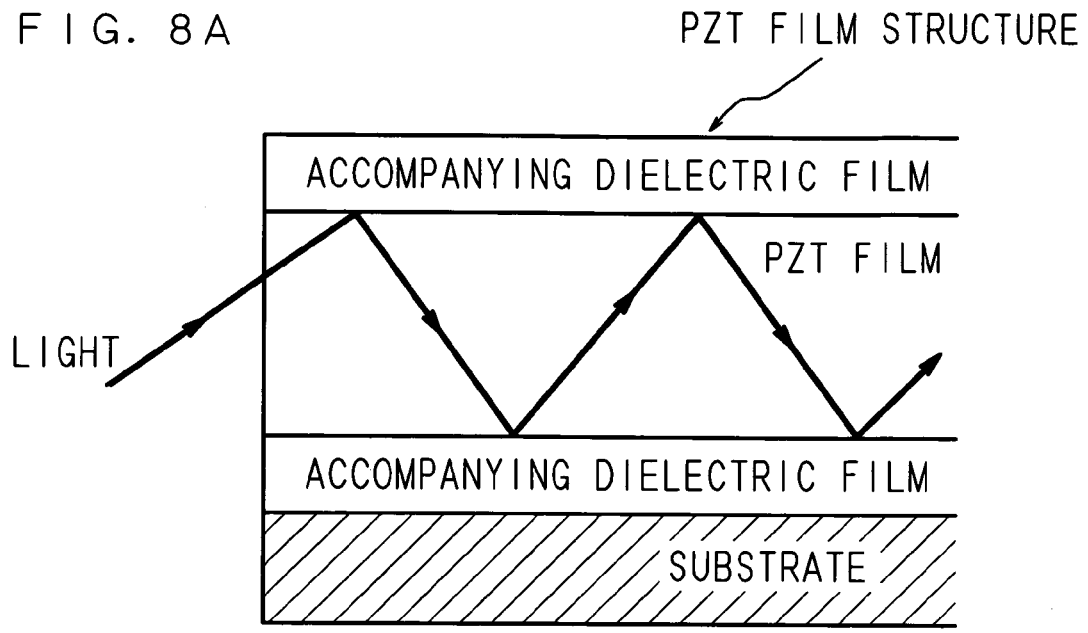
FIG. 8A is a schematic view showing the structure of a PZT film structure for totally reflecting light by a PZT film sandwiched between accompanying dielectric films.

FIG. 8A shows a PZT film structure, including accompanying dielectric films generated on the both sides of a PZT film, formed on the substrate and the film's surface, and this PZT film structure was formed based on a film forming condition determined, so that the refractive indices of the upper and lower accompanying dielectric films are smaller than the refractive index of the PZT film. Therefore, if light is applied from a side face of the PZT film of the PZT film structure, it is possible to achieve total reflection of the light by the upper and lower accompanying dielectric films and cause the light to travel in the PZT film.

Figure 8B:
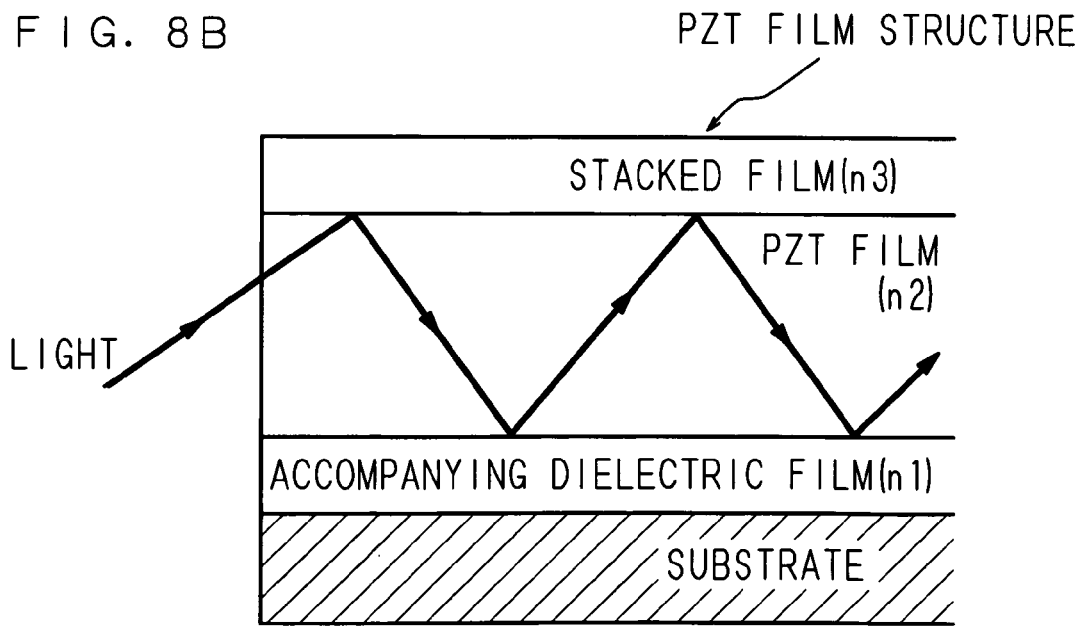
FIG. 8B is a schematic view showing the structure of a PZT film structure for totally reflecting light by a PZT film sandwiched between stacked and accompanying dielectric films.

FIG. 8B shows the case where a PZT film is formed on a substrate, a film having a smaller refractive index (n3), than the refractive index (n2) of the PZT film, is stacked on the PZT film, and a PZT film structure including an accompanying dielectric film, having a smaller refractive index (n1) than the refractive index (n2), is generated intentionally at the interface on the substrate side of the PZT film. Therefore, even in this PZT film structure, similarly to FIG. 8A, if light is applied from a side face of the PZT film, the incident light is totally reflected from both the stacked film on the film surface side and the accompanying dielectric film on the interface side, and the PZT film can be used as an optical waveguide.

The flow chart to determine a condition for forming a PZT film shown in FIGS. 8A and 8B is basically the same as the above-described method, but differs only in determining, whether or not to change the film forming condition, so as to keep an accompanying dielectric film, having an intended refractive index. In other words, the refractive index of the accompanying dielectric film, formed following the formation of the PZT film is obtained, by performing analysis with the spectroscopic ellipsometer, the obtained refractive index of the accompanying dielectric film and the refractive index of the PZT film are compared, and a determination is made from the comparison result as to whether or not to change the film forming condition variable.

A specific example of the content of the film forming condition determination method, in the above-mentioned case, will be explained with respect to the formation of a PZT film structure shown in FIG. 8B. First, a first prototype of a PZT film structure is produced by forming a PZT film with a refractive index n2, on a substrate by setting predetermined parameter values, and stacking an overlayer film with a refractive index n3 (n3<n2) on the PZT film, and then the refractive index of an accompanying dielectric film formed at the interface on the substrate side of the PZT film is obtained by performing analysis with a spectroscopic ellipsometer. Next, a second prototype of a PZT film structure is produced by forming a film in the same manner as above by setting values different from the above-mentioned parameter values, and the refractive index of an accompanying dielectric film formed at the interface on the substrate side of the PZT film is obtained by performing analysis with the spectroscopic ellipsometer.

Finally, by comparing the refractive index of the accompanying dielectric film of the first PZT film structure and the refractive index of the accompanying dielectric film of the second PZT film structure, a PZT film with the accompanying dielectric film having the refractive index n1 smaller than the refractive index n2 of the PZT film is selected, and the parameter values of the selected PZT film structure are determined as the film forming condition variables.

In the final comparison, if the refractive index of either of the accompanying dielectric films is not smaller than the refractive index of the PZT film, a PZT film structure with the accompanying dielectric film having a smaller refractive index is selected, and then the process of finding parameter values of a film forming condition, to make the refractive index of the accompanying dielectric film smaller than the refractive index of the PZT film, is performed, by repeating the above-mentioned method. On the other hand, in the final comparison, if the refractive index of either of the accompanying dielectric films is smaller than the refractive index of the PZT film, a PZT film structure having good characteristics as a whole is selected by taking other characteristics of the accompanying dielectric films into account.

Note that when a PZT film structure including an accompanying dielectric film is used in other applications, such as an application in which the light is not totally reflected, it is possible to apply a condition, other than the above-mentioned condition, to the determination concerning the refractive index, and it is also possible to determine a condition, concerning the formation of a PZT film structure, in which an intended predetermined accompanying dielectric film is present, based on characteristics other than the refractive index (such as the dielectric constant and the value of the film thickness).

Figure 9:
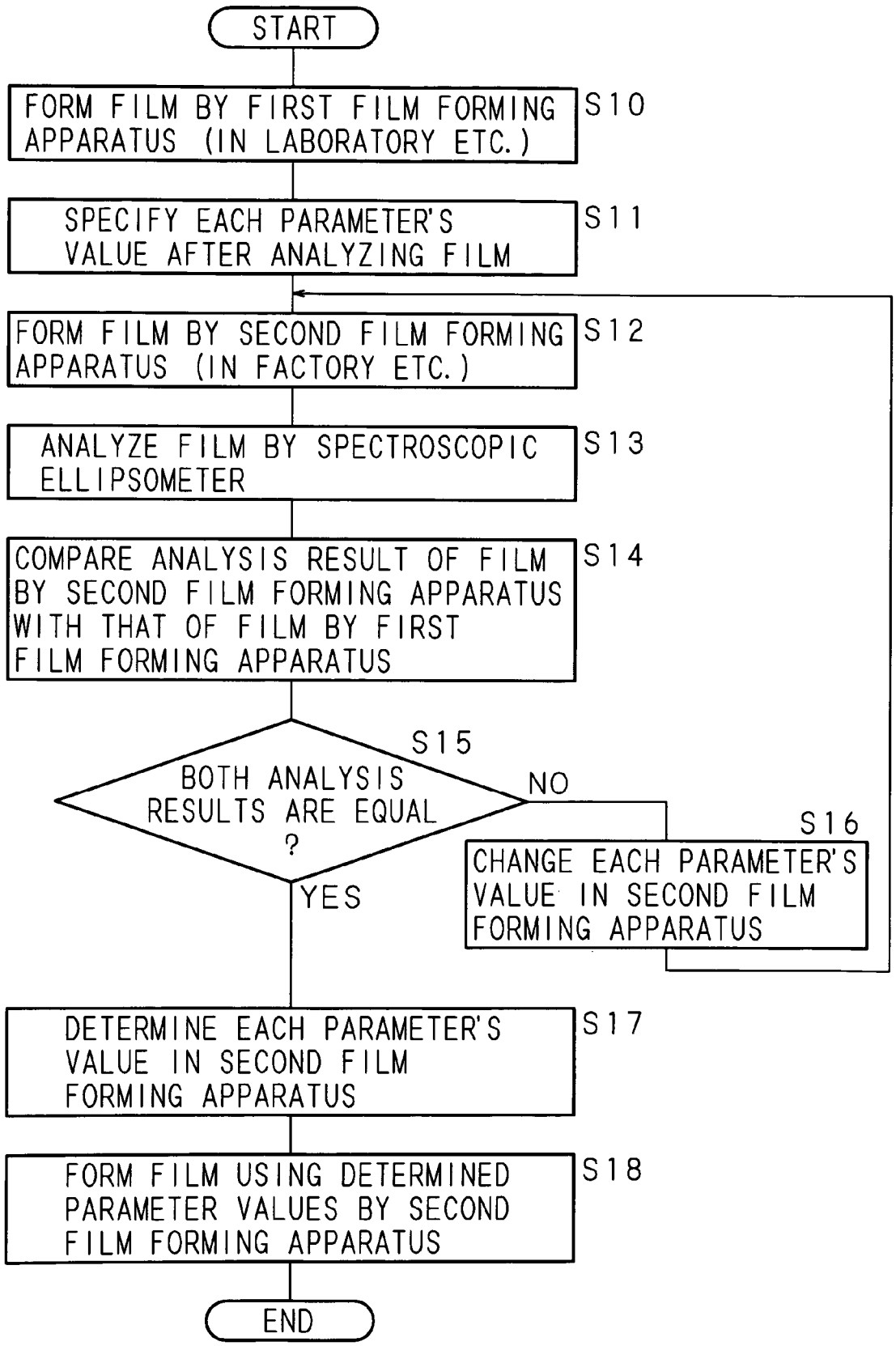
FIG. 9 is a flowchart showing the processing steps of a film forming method according to the second embodiment.

FIG. 9 is a flowchart showing the processing steps of a film forming method, according to the second embodiment of the present invention. The film forming method of the second embodiment is applied to shift a film structure formation, for which a film forming condition has been determined, using the film forming condition determination method of the first embodiment, to the mass-production stage.

If a film forming apparatus, for use in the mass-production stage, is a MOCVD apparatus, for example, its basic structure is the same, as the one shown in FIG. 3, but it is capable of accepting a plurality of substrates S on the mount base 6, so that a plurality of film structures can be formed by one film forming processing. Therefore, since the film forming apparatus for mass-production differs in the scale from the film forming apparatus used in the prototype production stage, an adjustment is made, using the film forming method of the present invention to match the film forming condition determined at the prototype production stage with the mass-production stage. Note that the film forming method of the second embodiment is applicable to both the film formation of a high dialectic film or ferroelectric film, such as PZT, whose dielectric constant based on electrical measurement is not lower than 50, and the film formation of a dielectric film, with a dielectric constant lower than the high-dielectric constant film.

The explanation will be given based on the flowchart of FIG. 9. First, film formation is performed by a first film forming apparatus, corresponding to the prototype production stage in a laboratory etc. (S10), and parameter values for an optimal film forming condition are specified by analyzing the film (S11). For the film formation using the first film forming apparatus (S10); and the specification of the respective parameter values (S11), if the film structure has a high-dielectric constant film or ferroelectric film formed on a substrate, it is preferable to apply the film forming condition determination method of the first embodiment, but if the film structure is used as a material for DRAM or the like, it may be possible to determine a film forming condition by electrical measurement.

Next, film formation is performed to form a similar film structure by a larger second film forming apparatus for use in the mass-production stage in a factory, etc. (S12). For the parameters concerning a film forming condition in the second film forming apparatus, although it is preferable to use temporarily the values corresponding to the respective parameter values, set in the first film forming apparatus, it may be possible to adjust the respective parameter values, corresponding to the first film forming apparatus based on the past prototype values, etc. and use the adjusted values.

Then, the analysis of the film in the film structure, formed by the second film forming apparatus, is performed by the spectroscopic ellipsometer 20 having the structure shown in FIG. 5 (S13). By using the spectroscopic ellipsometer in such a manner, it is possible to perform more efficient analysis compared with electrical measurement, and particularly, the application of the spectroscopic ellipsometer is essential for the analysis of the high-dielectric constant film or ferroelectric film, because it is necessary to analyze the accompanying dielectric film.

When the analysis is finished, the analysis result of the film, obtained by the second film forming apparatus, and the analysis result of the film obtained, by the first film forming apparatus are compared (S14), and a determination is made as to whether or not both the analysis results are equal (S15). The determination, as to whether or not both the analysis results are equal, is made, based on whether or not the analysis result of the film, obtained by the second film forming apparatus, is included in a predetermined range allowed in the specifications of the product, with respect to the analysis result of the film, obtained by the first film forming apparatus.

If these analysis results are not equal (S15: NO), the parameter values, concerning the film forming condition in the second film forming apparatus, are changed, so that the analysis result of the film, obtained by the second film forming apparatus, becomes closer to the analysis result of the film obtained by the first film forming apparatus (S16). When changing the parameter values, it is possible to use the film forming condition determination method described in the first embodiment.

When changing the parameter values, using the film forming condition determination method of the first embodiment, film formation is performed by setting two kinds of different parameter values for one parameter, and the resulting two film structures are respectively analyzed by the spectroscopic ellipsometer. Then, a determination is made as to which of the film structures formed, based on the two kinds of parameter values, is closer to the analysis result of the film obtained by the first film forming apparatus. The one with the result, closer to the analysis result of the film, obtained by the first film forming apparatus, is determined to have good film characteristics, and the parameter values corresponding to the good film characteristics are selected. Then, by performing the same processing one after another, a good parameter value is determined for one parameter, and other parameter values are selected in the same manner, due to change of the respective parameter values.

Moreover, when changing the parameter values, by using a film forming condition determination method corresponding to a modified example of the first embodiment, film formation is performed by setting a parameter value different from an initially set parameter value for one parameter, and the resulting one piece of film structure is analyzed using a spectroscopic ellipsometer. Then, a determination is made as to whether or not the analysis result is closer to the analysis result of the film obtained by the first film forming apparatus, and, if so, the newly set parameter value is selected. On the other hand, if the analysis result is not closer, a parameter value is varying in the opposite direction, to the newly set parameter value from the initially set parameter value, and the same processing as above is performed to specify a parameter value to get closer to the analysis result of the film, obtained by the first film forming apparatus. Further, the same processing is performed on other parameters to determine optimal parameter values and change the parameter values respectively.

After changing the respective parameter values, the changed parameter values are set, and film formation is performed by the second film forming apparatus (S12). Then, the processing steps from the film formation (S12) to changing of the parameter values (S16) are repeated until both the analysis results become equal.

On the other hand, when both the analysis results become equal (S15: YES), a determination is made to use the parameter values set in the second film forming apparatus at this time (S17), and mass-production of the film structure is performed by forming a film according to the determined parameter values by the second film forming apparatus (S18). Thus, by using the film forming method of the second embodiment, it is possible to shift smoothly to the mass-production stage. Moreover, even when the film structure to be formed by the film formation includes a low dielectric film, there is a merit that it is possible to reduce the number of mass-produced prototypes compared with electrical measurement, by using the spectroscopic ellipsometer for analyzing the film (S13) and changing the parameter values (S16).

Figure 10:
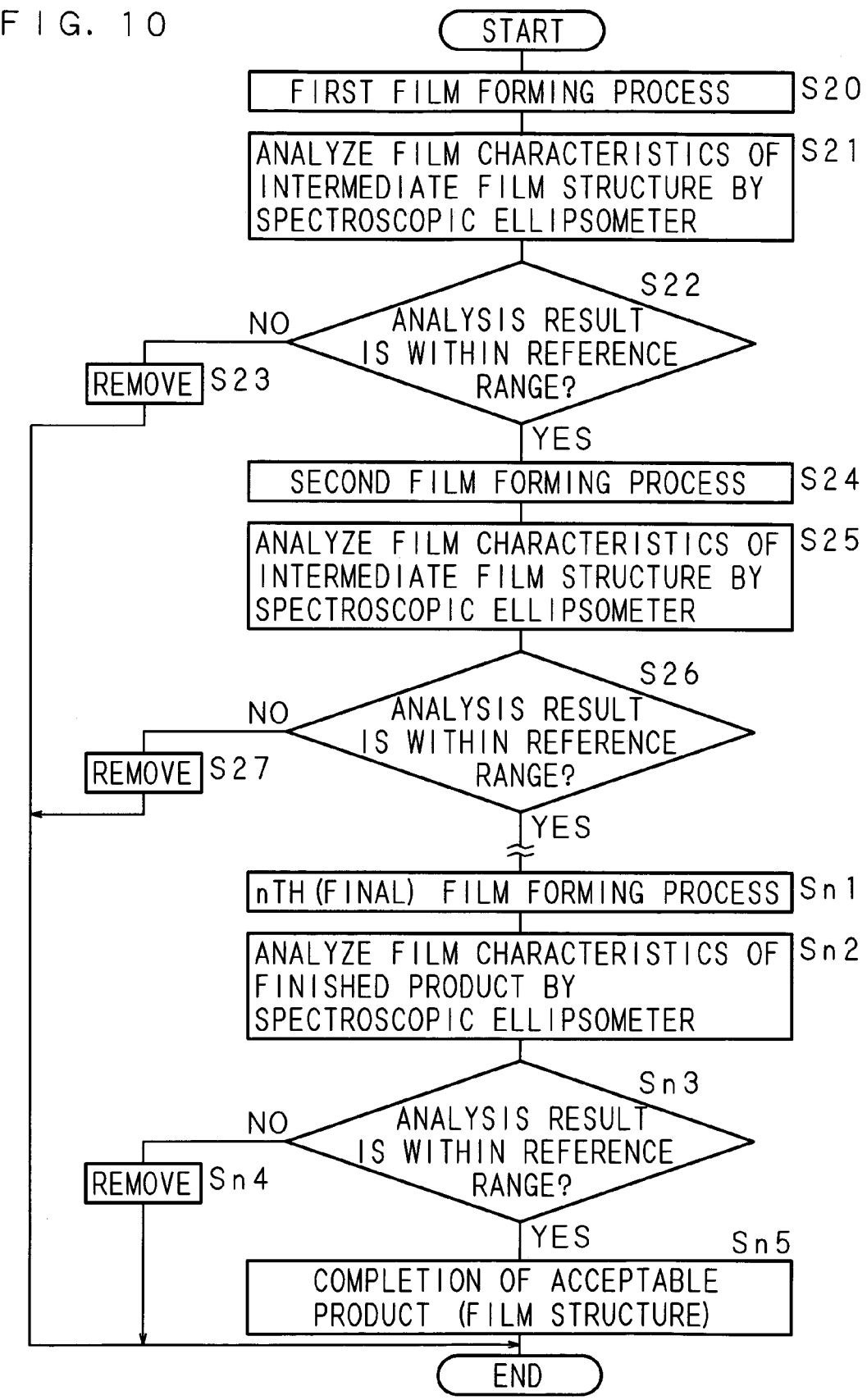
FIG. 10 is a flowchart showing the processing steps of a film structure manufacturing method according to the third embodiment.

FIG. 10 is a flowchart showing the processing steps of a film structure manufacturing method according to a third embodiment of the present invention. The film structure manufacturing method of the third embodiment aims at improving the yield by appropriately managing the quality of mass-production, when starting the mass-production of film structure by the film forming method of the second embodiment, etc. Although the formation of the film structure is performed through a plurality of film forming steps, the flowchart of FIG. 10 explains that the film structure is completed by the first film forming step through the nth film forming step (n is the number of final film forming step). Note that the number n varies depending on the kind of film structure to be formed. Suppose that, in each film forming step, a range (reference range) of the reference characteristic that is an allowed range for the film characteristic of an intermediate film structure in this step is predetermined.

As shown in the flowchart of FIG. 10, first, the first film forming process is performed (S20), and the film characteristics of the formed intermediate film structure is analyzed by a spectroscopic ellipsometer 20 having the structure shown in FIG. 5 (S21). A determination is made as to whether or not the analysis result is within the reference range (S22). If the analysis result is not within the reference range (S22: NO), the intermediate film structure is removed from the film forming process (S23), and the film forming process on the intermediate film structure is finished.

On the other hand, if the analysis result is within the reference range (S22: YES), the second film forming process is performed on the intermediate film structure (S24), the film characteristics are analyzed by the spectroscopic ellipsometer 20 (S25), and a determination is made as to whether or not the analysis result is within the reference range (S26). If the analysis result is not within the reference range (S26: NO), the intermediate film structure is removed from the film forming process (S27). Whereas, if the analysis result is within the reference range (S26: YES), the next film forming process is performed.

The nth (final) film forming process is performed through the same process as above (Sn1), the film characteristic of the finished product is analyzed by the spectroscopic ellipsometer (Sn2), and a determination is made as to whether or not the analysis result is within the reference range (Sn3). If the analysis result is not within the reference range (Sn3: NO), the finished product is removed as a defective product (Sn4). If the analysis result is within the reference range (Sn3: YES), an acceptable product (film structure) is completed (Sn5). Thus, since the next film forming process is not performed on an intermediate film structure determined to be defective, it is possible to improve the processing efficiency of the subsequent film forming steps and improve the yield of final finished product.

Figure 11:
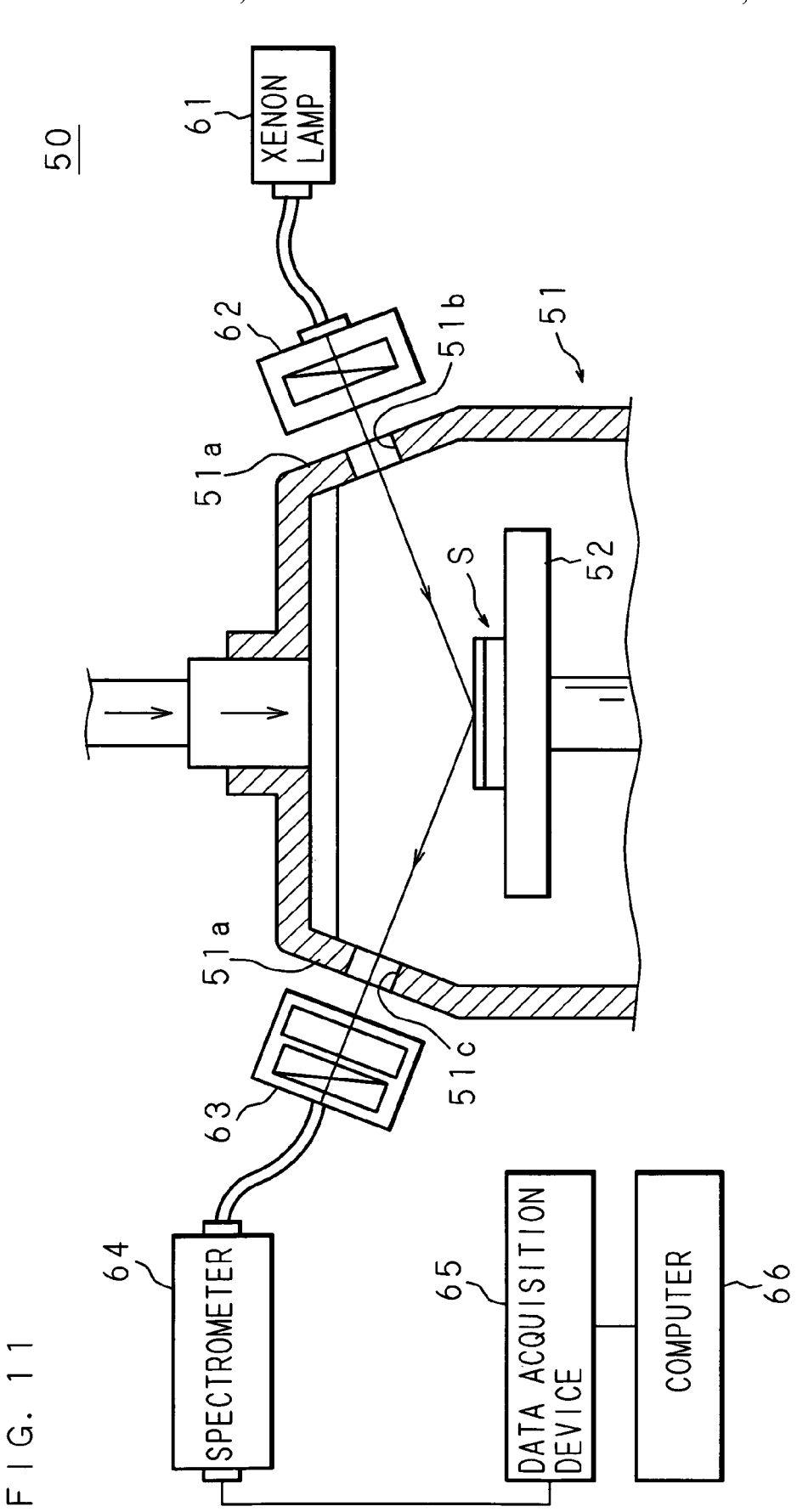
FIG. 11 is a schematic view showing the structure of a film formation analyzing apparatus.

FIG. 11 is a schematic view showing the structure of a film formation analyzing apparatus 50 that can be applied to the film structure manufacturing method of the third embodiment. The film formation analyzing apparatus 50 has a structure obtained by combining the film forming apparatus (MOCVD apparatus 1) shown in FIG. 3 and the spectroscopic ellipsometer 20 shown in FIG. 5. More specifically, heat resisting glasses 51b and 51c are fitted into sloping side walls 51a in a reaction chamber 51 in which a mount base 52 for mounting a substrate S is positioned, and a light polarizer 62 to which a xenon lamp 61 is connected is positioned outside first heat resisting glass 51b, so that light can be irradiated to the substrate S (film structure) through the heat resisting glass 51b. Note that the first heat resisting glass 51b is arranged orthogonally to the optical axis of light, irradiated by the light polarizer 62, and the other heat resisting glass 51c is arranged orthogonally to the optical axis of light reflected from the film structure. Moreover, a light receiver 63 to which a spectrometer 64 is connected is positioned outside the other heat resisting glass 51c so as to receive the reflected light. A data acquisition device 65 connected to a computer 66 is connected to the spectrometer 64.

With the use of such a film formation analyzing apparatus 50, since the film characteristics of an intermediate film structure before the film forming process, during the film forming process, and after the film forming process can be analyzed continuously with the film forming process, it is possible to perform the film structure manufacturing method of the third embodiment more efficiently. Note that the film structure manufacturing method of the third embodiment is, of course, applicable to the manufacture of a film structure by forming a high-dielectric constant film or ferroelectric film, whose dielectric constant is not lower than 50 based on electrical measurement, on a substrate, and is also applicable to the manufacture of a film structure by forming a dielectric film having a dielectric constant lower than the high-dielectric constant film or ferroelectric film on a substrate. In this case, it is also possible to improve the yield by analyzing the intermediate film structure in each film forming step with a spectroscopic ellipsometer.

As this invention may be embodied in several forms without departing from the spirit of essential characteristics thereof, the present embodiments are therefore illustrative and not restrictive, since the scope of the invention is defined by the appended claims rather than by the description preceding them, and all changes that fall within metes and bounds of the claims, or equivalence of such metes and bounds thereof are therefore intended to be embraced by the claims.

The invention claimed is:

1. A film forming condition determination method comprising the steps of:

forming a dielectric film, whose dielectric constant based on electrical measurement is not lower than 50, on a substrate by setting a predetermined value for a film forming condition variable;

analyzing a characteristic of the formed film by a spectroscopic ellipsometer;

comparing an analysis result with a reference characteristic value;

determining from a comparison result whether or not to change the predetermined value for the film forming condition variable; and determining a film forming condition by specifying a film forming value of the film forming condition variable as one of the predetermined value or a changed value based on the determination from the comparison result.

2. A film forming condition determination method comprising:
- a first step of forming a first dielectric film under a first film forming condition, whose dielectric constant based on electrical measurement is not lower than 50, on a first substrate by setting a predetermined value for a film forming condition variable;
- a second step of analyzing a characteristic of the first film formed in the first step by a spectroscopic ellipsometer;
- a third step of forming a second dielectric film under a second film forming condition, whose dielectric constant based on electrical measurement is not lower than 50, on a second substrate by setting a value different from the predetermined value set in the first step for the film forming condition variable;
- a fourth step of analyzing a characteristic of the second film formed in the third step by the spectroscopic ellipsometer; and
- a fifth step of specifying a value of the film forming condition variable, based on a comparison between an analysis result in the second step and an analysis result in the fourth step.

3. The film forming condition determination method according to claim 2, wherein in the second step and the fourth step, a film thickness of an accompanying dielectric film, formed on one side or both sides of each of the first or second films, following the formation of the respective first or second film, is analyzed and obtained by the spectroscopic ellipsometer, and in the fifth step, the obtained film thicknesses of the respective accompanying dielectric films formed on each of the first and second films are compared, and a value of the film forming condition variable corresponding to the formation of the accompanying dielectric film having a thinner film thickness is specified as a film forming value of the film forming condition variable.

4. The film forming condition determination method according to claim 2, wherein:
- in the first step and the third step, a first plurality of dielectric films are formed as layers on the first substrate under the first film forming condition and a second plurality of dielectric films are formed as layers on the second substrate under the second film forming condition, respectively,
- in each of the second step and the fourth step, a film thickness of an accompanying dielectric film formed between respective dielectric films in the first plurality of dielectric films and the second plurality of dielectric films, respectively, following the formation of said respective plurality of dielectric films, is analyzed and obtained by the spectroscopic ellipsometer, and
- in the fifth step, the obtained film thicknesses of the respective accompanying dielectric films are compared, and a value corresponding to the formation of accompanying dielectric film, having a thinner film thickness, is specified as a value of the film forming condition variable.

5. A film forming condition determination method comprising the steps of:
- forming a dielectric film, whose dielectric constant based on electrical measurement is not lower than 50, on a substrate by setting a predetermined value for a film forming condition variable;
- analyzing and obtaining a refractive index of an accompanying dielectric film, formed on one side or both sides of the dielectric film, following the formation of the dielectric film, by a spectroscopic ellipsometer;
- comparing the obtained refractive index of the accompanying dielectric film and a refractive index of the dielectric film;
- determining from a comparison result, whether or not to change the predetermined values for the film forming condition variable; and
- determining a film forming condition by specifying a film forming value of the film forming condition variable as one of the predetermined values or a changed value based on the determination from the comparison result.

6. A film forming condition determination method comprising:
- a first step of forming a first dielectric film under a first film forming condition, whose dielectric constant based on electrical measurement is not lower than 50, on a first substrate, by setting a predetermined value for a film forming condition variable, and stacking a first accompanying film, whose refractive index is smaller than the first dielectric film;
- a second step of analyzing and obtaining a refractive index of the first accompanying dielectric film, formed at the interface on the substrate side, following the formation of the first dielectric film in the first step, by a spectroscopic ellipsometer;
- a third step of forming a second dielectric film under a second film forming condition, whose dielectric constant based on electrical measurement is not lower than 50, on a second substrate, and stacking a second accompanying film whose refractive index is smaller than the second dielectric film on the second dielectric film, by setting a value different from the predetermined value set in the first step for the film forming condition variable;
- a fourth step of analyzing and obtaining a refractive index of the second accompanying dielectric film, formed at the interface on the substrate side, following the formation of the second dielectric film in the third step, by the spectroscopic ellipsometer; and
- a fifth step of specifying a value of the film forming condition variable by comparing the refractive index of the first accompanying dielectric film obtained in the second step and the refractive index of the second accompanying dielectric film obtained in the fourth step.

7. A film forming method comprising:
- a first step of forming a film by a first film forming apparatus, by setting a predetermined value for a film forming condition variable in the first film forming apparatus;
- a second step of analyzing a characteristic of the film formed in the first step;
- a third step of forming a film by a second film forming apparatus by setting a value corresponding to the predetermined value set in the first film forming apparatus for a film forming condition variable in the second film forming apparatus;
- a fourth step of analyzing a characteristic of the film formed in the third step by a spectroscopic ellipsometer;
- a fifth step of comparing an analysis result in the second step and an analysis result in the fourth step to determine whether the analysis results differ,
- a sixth step, when the analysis results differ, of specifying a revised value of the film forming condition variable to be set in the second film forming apparatus so that the analysis result in the fourth step becomes closer to the analysis result in the second step; and
- a seventh step of forming a film by the second film forming apparatus, when the analysis results differ, by setting the revised value specified in the sixth step for the film forming condition variable in the second film forming apparatus.

8. The film forming method according to claim 7, wherein the first film forming apparatus and the second film forming apparatus perform film formation by forming a dielectric film whose dielectric constant based on electrical measurement is not lower than 50 on the substrate.

9. The film forming method according to claim 8, wherein in the sixth step, a value of the film forming condition variable is specified using a film forming condition determination method comprising the steps of:
   forming a dielectric film, whose dielectric constant based on electrical measurement is not lower than 50, on a substrate by setting a predetermined value for a film forming condition variable;
   analyzing a characteristic of the formed film by a spectroscopic ellipsometer;
   comparing an analysis result with a reference characteristic value;
   determining from a comparison result whether or not to change the predetermined value for the film forming condition variable; and
   determining a film forming condition by specifying a film forming value of the film forming condition variable as one of the predetermined value or a changed value based on the determination from the comparison result.

10. The film forming method according to claim 8, wherein in the sixth step, a value of the film forming condition variable is specified using a film forming condition determination method comprising:
   a first step of forming a first dielectric film under a first film forming condition, whose dielectric constant based on electrical measurement is not lower than 50, on a first substrate by setting a predetermined value for a film forming condition variable;
   a second step of analyzing a characteristic of the first film formed in the first step by a spectroscopic ellipsometer;
   a third step of forming a second dielectric film under a second film forming condition, whose dielectric constant based on electrical measurement is not lower than 50, on a second substrate by setting a value different from the predetermined value set in the first step for the film forming condition variable;
   a fourth step of analyzing a characteristic of the second film formed in the third step by the spectroscopic ellipsometer; and
   a fifth step of specifying a value of the film forming condition variable, based on a comparison between an analysis result in the second step and an analysis result in the fourth step.

11. The film forming method according to claim 8, wherein in the sixth step, a value of the film forming condition variable is specified using a film forming condition determination method comprising the steps of:
   forming a dielectric film, whose dielectric constant based on electrical measurement is not lower than 50, on a substrate by setting a predetermined value for a film forming condition variable;
   analyzing and obtaining a refractive index of an accompanying dielectric film, formed on one side or both sides of the dielectric film, following the formation of the dielectric film, by a spectroscopic ellipsometer;
   comparing the obtained refractive index of the accompanying dielectric film and a refractive index of the dielectric film;
   determining from a comparison result, whether or not to change the predetermined values for the film forming condition variable; and
   determining a film forming condition by specifying a film forming value of the film forming condition variable as one of the predetermined values or a changed value based on the determination from the comparison result.

12. The film forming method according to claim 8, wherein in the sixth step, a value of the film forming condition variable is specified using the film forming condition determination method comprising:
   a first step of forming a first dielectric film under a first film forming condition, whose dielectric constant based on electrical measurement is not lower than 50, on a first substrate, by setting a predetermined value for a film forming condition variable, and stacking a first accompanying film, whose refractive index is smaller than the first dielectric film;
   a second step of analyzing and obtaining a refractive index of the first accompanying dielectric film, formed at the interface on the substrate side, following the formation of the first dielectric film in the first step, by a spectroscopic ellipsometer;
   a third step of forming a second dielectric film under a second film forming condition, whose dielectric constant based on electrical measurement is not lower than 50, on a second substrate, and stacking a second accompanying film whose refractive index is smaller than the second dielectric film on the second dielectric film, by setting a value different from the predetermined value set in the first step for the film forming condition variable;
   a fourth step of analyzing and obtaining a refractive index of the second accompanying dielectric film, formed at the interface on the substrate side, following the formation of the second dielectric film in the third step, by the spectroscopic ellipsometer; and
   a fifth step of specifying a value of the film forming condition variable by comparing the refractive index of the first accompanying dielectric film obtained in the second step and the refractive index of the second accompanying dielectric film obtained in the fourth step.

13. The film forming condition determination method according to claim 1, including a film structure manufacturing method for manufacturing a film structure by performing a plurality of film forming steps one after another each producing an intermediate film structure, the film structure manufacturing method further comprising the steps of:
   analyzing a characteristic of the intermediate film structure processed in each film forming step by a spectroscopic ellipsometer;
   determining whether or not the analyzed characteristic is within a reference characteristic range, corresponding to the intermediate film structure; and
   processing the intermediate film structure, determined to have a characteristic within the reference characteristic range, in a next one of the plurality of film forming steps.

14. The film structure manufacturing method according to claim 13, wherein each intermediate film structure formed by the plurality of film forming steps comprises a dielectric film whose dielectric constant based on electrical measurement is not lower than 50.

15. The film forming condition determination method according to claim 2, including a film structure manufacturing method for manufacturing a film structure by performing a plurality of first steps of forming a film under the first forming condition or a plurality of third steps of forming a film under the second film forming condition, one after another each producing an intermediate film structure, the film structure manufacturing method further comprising the steps of:

analyzing a characteristic of the intermediate film structure processed in one of the plurality of first steps of forming a film under the first forming condition or one of the plurality of third steps of forming a film under the second film forming condition, by a spectroscopic ellipsometer;

determining whether or not the analyzed characteristic is within a reference characteristic range, corresponding to the intermediate film structure; and processing the intermediate film structure, determined to have a characteristic within the reference characteristic range, in a respective next one of the plurality of first steps of film forming under the first forming condition or in a next one of the plurality of third steps of film forming under the second film forming condition.

16. The film structure manufacturing method according to claim 15, wherein the intermediate film structure formed by the plurality of first or third film forming steps comprises a dielectric film whose dielectric constant based on electrical measurement is not lower than 50.

17. The film forming condition determination method according to claim 5, including a film structure manufacturing method for manufacturing a film structure by performing a plurality of film forming steps one after another each producing an intermediate film structure, the film structure manufacturing method further comprising the steps of:

analyzing a characteristic of the intermediate film structure processed in each film forming step, by a spectroscopic ellipsometer;

determining whether or not the analyzed characteristic is within a reference characteristic range, corresponding to the intermediate film structure; and processing the intermediate film structure, determined to have a characteristic within the reference characteristic range, in a next one of the plurality of film forming steps.

18. The film structure manufacturing method according to claim 17, wherein each intermediate film structure formed by the plurality of film forming steps comprises a dielectric film whose dielectric constant based on electrical measurement is not lower than 50.

19. The film forming condition determination method according to claim 6, applied to a film structure manufacturing method for manufacturing a film structure by performing a plurality of first steps of forming a film one after another each producing an intermediate film structure, the film structure manufacturing method further comprising the steps of:

analyzing a characteristic of the intermediate film structure processed in each first step of forming a film, by a spectroscopic ellipsometer;

determining whether or not the analyzed characteristic is within a reference characteristic range, corresponding to the intermediate film structure; and processing the intermediate film structure, determined to have a characteristic within the reference characteristic range, in a next one of the plurality of first steps of film forming.

20. The film structure manufacturing method according to claim 19, wherein each intermediate film structure formed by the plurality of film forming steps comprises a dielectric film whose dielectric constant based on electrical measurement is not lower than 50.

* * * * *